US012733961B2

(12) United States Patent
Serra et al.

(10) Patent No.: US 12,733,961 B2

(45) **Date of Patent: *Sep. 15, 2026**

(54) SURGICAL CORD TENSIONING DEVICES, SYSTEMS, AND METHODS

(71) Applicant: Highridge Medical, LLC, Westminster, CO (US)

(72) Inventors: Thomas Serra, Arvada, CO (US); Randall G. Mast, Denver, CO (US)

(73) Assignee: Highridge Medical, LLC, Westminster, CO (US)

(*) Notice: Subject to any disclaimer, the term of this patent is extended or adjusted under 35 U.S.C. 154(b) by 347 days.

This patent is subject to a terminal disclaimer.

(21) Appl. No.: 18/330,595

(22) Filed: Jun. 7, 2023

(65) Prior Publication Data

US 2023/0310042 A1 Oct. 5, 2023

Related U.S. Application Data

(63) Continuation of application No. 17/164,447, filed on Feb. 1, 2021, which is a continuation of application (Continued)

(51) Int. Cl.

| | |
|---|---|
| ***A61B 17/70*** | (2006.01) |
| ***A61B 17/88*** | (2006.01) |
| *A61B 90/00* | (2016.01) |

(52) U.S. Cl.

CPC ...... *A61B 17/7083* (2013.01); *A61B 17/7022* (2013.01); *A61B 17/7085* (2013.01); (Continued)

(58) Field of Classification Search

CPC ............ A61B 17/7083; A61B 17/7085; A61B 17/7086; A61B 17/7088; A61B 17/7089; (Continued)

(56) References Cited

U.S. PATENT DOCUMENTS

| | | | |
|---|---|---|---|
| 5,423,848 | A | 6/1995 | Washizuka et al. |
| 6,251,111 | B1 | 6/2001 | Barker et al. |

(Continued)

FOREIGN PATENT DOCUMENTS

| | | |
|---|---|---|
| EP | 2047813 | 4/2009 |
| FR | 2777449 | 10/1999 |

(Continued)

OTHER PUBLICATIONS

"International Application Serial No. PCT/US2018/048403, International Search Report mailed Nov. 15, 2018", 5 pgs.

(Continued)

*Primary Examiner* — Jan Christopher L Merene

(57) ABSTRACT

A system, a method, and instruments for manipulating a surgical cord into spinal implants to assist in correcting a spinal deformity are described. The system may include a tensioner, a tensioner extension, and a counter tensioner. One of the instruments can include an elongate body, a dual coupler, and a nose member. The elongate body has a flexible cylindrical member adapted to carry tension along a longitudinal axis, where the flexible cylindrical member is sized to receive a surgical cord through a lumen within the flexible cylindrical member. The dual coupler is disposed on a proximal end of the elongate body, and include a bore for receiving a nose portion of a tensioner and for guiding the surgical cord into the tensioner. The nose member is disposed on a distal end of the elongate body, and be adapted to discharge the surgical cord from the elongate body.

22 Claims, 20 Drawing Sheets

Related U.S. Application Data

No. 16/156,158, filed on Oct. 10, 2018, now Pat. No. 10,939,941, which is a continuation-in-part of application No. 16/115,441, filed on Aug. 28, 2018, now Pat. No. 10,905,474.

(60) Provisional application No. 62/551,379, filed on Aug. 29, 2017.

(52) U.S. Cl.
CPC ...... *A61B 17/7091* (2013.01); *A61B 17/8869* (2013.01); *A61B 17/7053* (2013.01); *A61B 2090/064* (2016.02)

(58) Field of Classification Search
CPC ............ A61B 17/8869; A61B 17/7022; A61B 17/7079; A61B 17/708; A61B 17/7082
See application file for complete search history.

(56) References Cited

U.S. PATENT DOCUMENTS

| | | | |
|---|---|---|---|
| 6,296,643 | B1 | 10/2001 | Hopf et al. |
| 7,073,415 | B2 | 7/2006 | Casutt et al. |
| 7,083,621 | B2 | 8/2006 | Shaolian et al. |
| 7,556,630 | B2 | 7/2009 | Molz et al. |
| 7,909,826 | B2 | 3/2011 | Serhan et al. |
| 7,909,857 | B2 | 3/2011 | Ogilvie et al. |
| 8,118,841 | B2 | 2/2012 | Schwab |
| 8,123,749 | B2 | 2/2012 | Serhan et al. |
| 8,273,086 | B2 | 9/2012 | Serhan et al. |
| 8,308,771 | B2 | 11/2012 | Bennett et al. |
| 8,337,528 | B2 | 12/2012 | Ferree |
| 8,454,662 | B2 | 6/2013 | Bethell |
| 8,465,526 | B2 | 6/2013 | Friedrich et al. |
| 8,562,653 | B2 | 10/2013 | Alamin et al. |
| 8,591,560 | B2 | 11/2013 | Jackson |
| 8,632,572 | B2 | 1/2014 | Darst Rice et al. |
| 8,641,736 | B2 | 2/2014 | Marik et al. |
| 8,764,803 | B2 | 7/2014 | Suddaby |
| 8,888,818 | B2 | 11/2014 | Serhan et al. |
| 8,992,578 | B2 | 3/2015 | Slivka et al. |
| 9,011,498 | B2 | 4/2015 | Ogilvie et al. |
| 9,039,711 | B2 | 5/2015 | Mickiewicz et al. |
| 9,101,408 | B1 | 8/2015 | Dix |
| 9,211,142 | B2 | 12/2015 | Friedrich et al. |
| 9,277,940 | B2 | 3/2016 | Rice |
| 9,339,297 | B2 | 5/2016 | Friedrich et al. |
| 9,370,390 | B2 | 6/2016 | Mickiewicz et al. |
| 9,492,165 | B2 | 11/2016 | Serhan et al. |
| 9,526,525 | B2 | 12/2016 | Remington et al. |
| 9,782,203 | B2 | 10/2017 | Rice et al. |
| 9,833,275 | B2 | 12/2017 | Mickiewicz et al. |
| 10,856,910 | B2 | 12/2020 | Rice et al. |
| 10,905,474 | B2 | 2/2021 | Mast |
| 10,939,941 | B2 | 3/2021 | Serra et al. |
| 11,690,656 | B2 | 7/2023 | Serra et al. |
| 2002/0032450 | A1 | 3/2002 | Trudeau et al. |
| 2005/0010220 | A1 | 1/2005 | Casutt et al. |
| 2007/0021737 | A1 | 1/2007 | Lee |
| 2007/0093846 | A1 | 4/2007 | Frigg et al. |
| 2007/0213714 | A1 | 9/2007 | Justis |
| 2008/0009863 | A1 | 1/2008 | Bond et al. |
| 2008/0077138 | A1 | 3/2008 | Cohen et al. |
| 2008/0132933 | A1 | 6/2008 | Gerber |
| 2008/0243052 | A1 | 10/2008 | Pond et al. |
| 2008/0262551 | A1 | 10/2008 | Rice et al. |
| 2008/0287951 | A1 | 11/2008 | Stoneburner et al. |
| 2009/0054933 | A1 | 2/2009 | Mickiewicz et al. |
| 2009/0082776 | A1 | 3/2009 | Cresina |
| 2009/0088799 | A1 | 4/2009 | Yeh |
| 2009/0163962 | A1 | 6/2009 | Dauster et al. |
| 2009/0198281 | A1 | 8/2009 | Rice et al. |
| 2010/0042106 | A1 | 2/2010 | Bryant et al. |
| 2010/0168803 | A1 | 7/2010 | Hestad et al. |
| 2010/0318137 | A1 | 12/2010 | Stucki et al. |
| 2011/0060367 | A1 | 3/2011 | Stauber |
| 2011/0184473 | A1 | 7/2011 | Garcia-Bengochea et al. |
| 2012/0221054 | A1 | 8/2012 | Jackson |
| 2012/0259374 | A1 | 10/2012 | Marik et al. |
| 2014/0243907 | A1 | 8/2014 | Cavallazzi et al. |
| 2014/0257416 | A1* | 9/2014 | Meyer ................ A61B 17/7083 606/86 A |
| 2014/0276051 | A1 | 9/2014 | Hoffman |
| 2015/0066042 | A1 | 3/2015 | Cummins et al. |
| 2015/0127003 | A1 | 5/2015 | Songer et al. |
| 2015/0209077 | A1 | 7/2015 | Marshall |
| 2015/0313644 | A1 | 11/2015 | Rice et al. |
| 2015/0342654 | A1 | 12/2015 | Gephart |
| 2016/0000468 | A1 | 1/2016 | Samdani et al. |
| 2016/0074147 | A1 | 3/2016 | Pereira et al. |
| 2016/0262811 | A1 | 9/2016 | Mickiewicz et al. |
| 2017/0027616 | A1 | 2/2017 | Serhan et al. |
| 2017/0172633 | A1 | 6/2017 | Simpson |
| 2017/0354445 | A1* | 12/2017 | Deneuvillers ...... A61B 17/7083 |
| 2018/0014856 | A1 | 1/2018 | Rice et al. |
| 2018/0029824 | A1 | 2/2018 | Gephart et al. |
| 2018/0110544 | A1* | 4/2018 | Simpson ............ A61B 17/7053 |
| 2019/0059958 | A1 | 2/2019 | Mast |
| 2019/0059959 | A1 | 2/2019 | Serra et al. |
| 2019/0262039 | A1 | 8/2019 | Gordon et al. |
| 2019/0336182 | A1 | 11/2019 | Suh et al. |
| 2020/0179012 | A1 | 6/2020 | Rice et al. |
| 2021/0121208 | A1 | 4/2021 | Mast |

FOREIGN PATENT DOCUMENTS

| | | |
|---|---|---|
| WO | WO 2019/046339 | 3/2019 |
| WO | WO 2020/077029 | 4/2020 |

OTHER PUBLICATIONS

"International Application Serial No. PCT/US2018/048403, Written Opinion mailed Nov. 15, 2018", 10 pgs.
"International Application Serial No. PCT/US2018/048403, International Preliminary Report on Patentability mailed Mar. 12, 2020", 12 pgs.
"International Application Serial No. PCT/US2019/055511, International Search Report mailed Jan. 21, 2020", 7 pgs.
"International Application Serial No. PCT/US2019/055511, Written Opinion mailed Jan. 21, 2020", 10 pgs.
"International Application Serial No. PCT/US2019/055511, International Preliminary Report on Patentability mailed Apr. 22, 2021", 12 pages.
"Australian Application Serial No. 2018323471, First Examination Report mailed Jun. 15, 2020", 7 pgs.
"Australian Application Serial No. 2018323471, Response filed Aug. 27, 2020 to First Examination Report mailed Jun. 15, 2020", 19 pgs.
Notice of Allowance for Australian Patent Application No. 2018323471, dated Sep. 29, 2020 3 pages.
Official Action for Australian Patent Application No. 2019358075, dated Sep. 21, 2021 4 pages.
Official Action for Australian Patent Application No. 2019358075, dated Nov. 30, 2021 4 pages.
Notice of Acceptance for Australian Patent Application No. 2019358075, dated Mar. 2, 2022 3 pages.
Official Action for Canadian Patent Application No. 3115479, dated Jun. 30, 2022 8 pages.
"European Application Serial No. 18766509.6, Response to Communication pursuant to Rules 161(1) and 162 EPC filed Oct. 19, 2020", 10 pgs.
Decision to Grant for European Application No. 18766509.6, dated Oct. 28, 2021 2 pages.
"U.S. Appl. No. 16/156,158, Non Final Office Action mailed Mar. 25, 2020", 15 pgs.
"U.S. Appl. No. 16/156,158, Non Final Office Action mailed Jul. 21, 2020", 15 pgs.

(56) References Cited

OTHER PUBLICATIONS

"U.S. Appl. No. 16/156,158, Notice of Allowance mailed Nov. 3, 2020", 8 pgs.
"U.S. Appl. No. 16/156,158, Response filed Jun. 24, 2020 to Non Final Office Action mailed Mar. 25, 2020", 14 pgs.
"U.S. Appl. No. 16/156,158, Response filed Oct. 21, 2020 to Non Final Office Action mailed Jul. 21, 2020", 10 pgs.
"U.S. Appl. No. 17/164,447, Preliminary Amendment filed Mar. 4, 2021", 6 pgs.
Official Action for U.S. Appl. No. 17/164,447, dated Nov. 9, 2022 10 pages.
Notice of Allowance for U.S. Appl. No. 17/164,447, dated Feb. 23, 2023 5 pages.
Intention to Grant for European Patent Application No. 19794394.7, dated Sep. 12, 2023 57 pages.

* cited by examiner

SURGICAL CORD TENSIONING DEVICES, SYSTEMS, AND METHODS

CLAIM OF PRIORITY

This application is a continuation of U.S. patent application Ser. No. 17/164,447, filed Feb. 1, 2021; which is a continuation of U.S. patent application Ser. No. 16/156,158, filed Oct. 10, 2018, now U.S. Pat. No. 10,939,941, issued on Mar. 9, 2021; which is a continuation-in-part of U.S. patent application Ser. No. 16/115,441, filed Aug. 28, 2018, now U.S. Pat. No. 10,905,474, issued Feb. 2, 2021; which claims the benefit of priority under 35 U.S.C. § 119(e) of U.S. Provisional Patent Application No. 62/551,379, filed Aug. 29, 2017; all of which are hereby incorporated by reference in their entireties.

BACKGROUND

Dynamic stabilization techniques, such as vertebral body tethering, are used in spinal treatment procedures for juveniles to permit enhanced mobility of the spine while also providing sufficient counter loading of a spinal curvature to effect treatment through bone growth modulation, particularly during times of rapid growth. Such dynamic stabilization systems may include pedicle screws installed in adjacent or nearby vertebrae of the spine and a flexible cord secured to the heads of the pedicle screws by set screws, with the cord under tension between pedicle screws.

SUMMARY

The present inventors have recognized, among other things, that improving ergonomics and ease of use of surgical cord (tether) tensioning devices, including improving access to remote implants, may be desirable. The present inventors have also recognized that decreasing the time to tension and secure the surgical cord in each implant can improve outcomes and decrease surgeon fatigue. The present specification discloses various methods, devices, systems, and embodiments that may include a cord tensioner that can be rigidly, removably coupleable to a coupler disposed on a proximal end of a counter tensioner, wherein the distal end of the counter tensioner can be rigidly, removably coupleable to a head of an implant. Additionally, the present specification discloses various tensioner extensions that can be used to position and tension a surgical cord (tether) from an auxiliary or secondary incision offset (usually inferiorly) from the spinal deformity being corrected. Accordingly, the present disclosure provides for a system for positioning and tensioning the surgical cord (tether) without repeated threading the cord through various surgical ports (incisions). The system may comprise a tensioner, a tensioner extension, and a counter tensioner. The tensioner can comprise a nose assembly and a cord lock assembly for applying tension to the cord. The nose assembly can comprise a piston having a lumen extending therethrough for receiving the cord and a spring positionable in contact with an indicator region of the piston. The tensioner extension can include one or more elongate extension members that can accommodate the cord through an internal lumen and couple to the nose of the tensioner. The counter tensioner can be releasably coupleable to a head of an implant at a distal end thereof and can guide a set screw into the implant to secure the cord. The counter tensioner may also enable translation of the implant relative to another implant implanted in an adjacent or nearby vertebrae. Further, the counter tensioner can be utilized as described in co-pending application Ser. No. 16/115,441, Titled "SURGICAL CORD TENSIONING DEVICES, SYSTEMS, AND METHOD," filed Aug. 28, 2018, which is hereby incorporated by reference in its entirety.

In an embodiment, the present disclosure discusses a method for positioning and tensioning a surgical cord using a secondary (auxiliary) surgical port and a tensioner extension threaded over the cord. In this embodiment, the cord is initially secured in a first implant with the cord subsequently routed through the body to the secondary surgical port. The cord is then threaded through the tensioner extension, and the tensioner extension is maneuvered into the body adjacent to a second implant. The tensioner extension, in combination with the counter tensioner or other instruments, is used to position the cord in the second implant. Once in the second implant, the tensioner can be coupled to the proximal end of the tensioner extension, and utilized to tension the cord between the first implant and the second implant. Once tensioned, the cord can be secured with a set screw delivered through the counter tensioner instrument. Upon completion of securing the cord to the second implant, the tensioner extension can maneuver the cord into a third implant and repeat steps to tension and secure the cord in the third implant. This process can be repeated for all implants being used to correct the spinal deformity.

In another embodiment, the present disclosure provides for a method that can include the steps of inserting a counter tensioner into a patient and coupling the counter tensioner to an implant; coupling a nose assembly of a tensioner to a port of the counter tensioner; guiding a cord through the counter tensioner and securing the cord therein; tensioning the cord by actuating a shaft clutch to translate the elongate shaft and the cord; preventing proximal travel of the elongate shaft and cord via engagement of a shaft lock; and translating the implant relative to an implant in an adjacent or nearby bone.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Exemplary embodiments will now be described more fully with reference to the accompanying drawings. Within the following disclosure the terms proximal and distal are generally used with reference to the surgeon using the instruments, rather than with respect to the patient. However, in description of certain examples the use of the terms may be inverted to correspond to the patient point of view.

The initial portion of the present disclosure provides for a system comprising a cord tensioner that can be rigidly, removably coupleable to a port disposed on a proximal end of a counter tensioner, wherein the distal end of the counter tensioner can be rigidly, removably coupleable to a head of an implant. Such systems and methods of using the system can improve ergonomics and ease of use by, e.g., enabling one handed operation of a tensioner. Such systems can also increase cord travel per actuation cycle of the cord tensioner and provide a visual indication of cord load during cord tensioning. FIGS. 1-7G address the system comprising only the cord tensioner and the counter tensioner. The remaining portion of the disclosure discusses the system utilizing the tensioner extension to facilitate an improved method of securing a surgical cord (tether) between implants to correct a spinal deformity.

Figure 1:
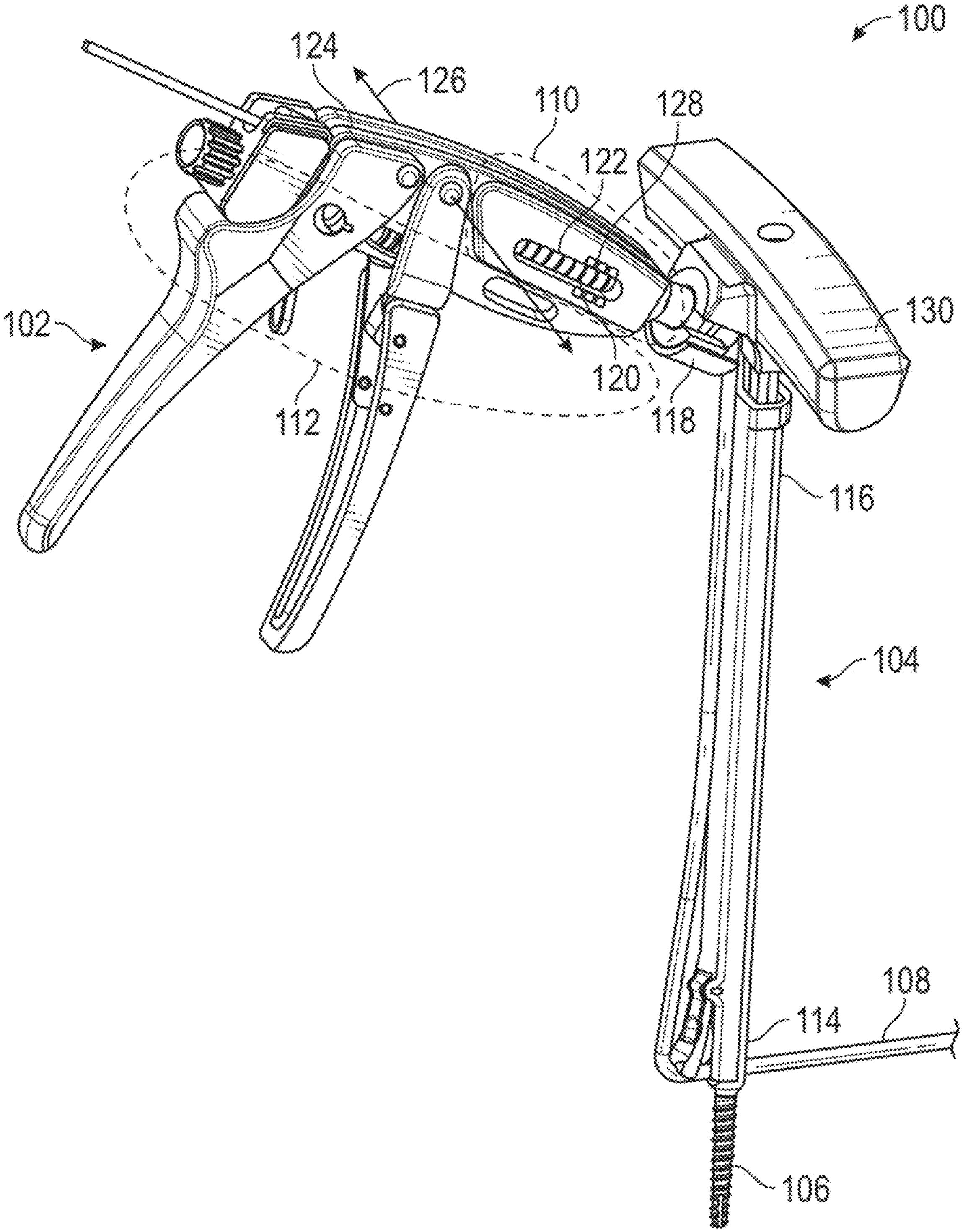
FIG. 1 is a perspective view of an embodiment of a system according to the present disclosure.
Figure 2:
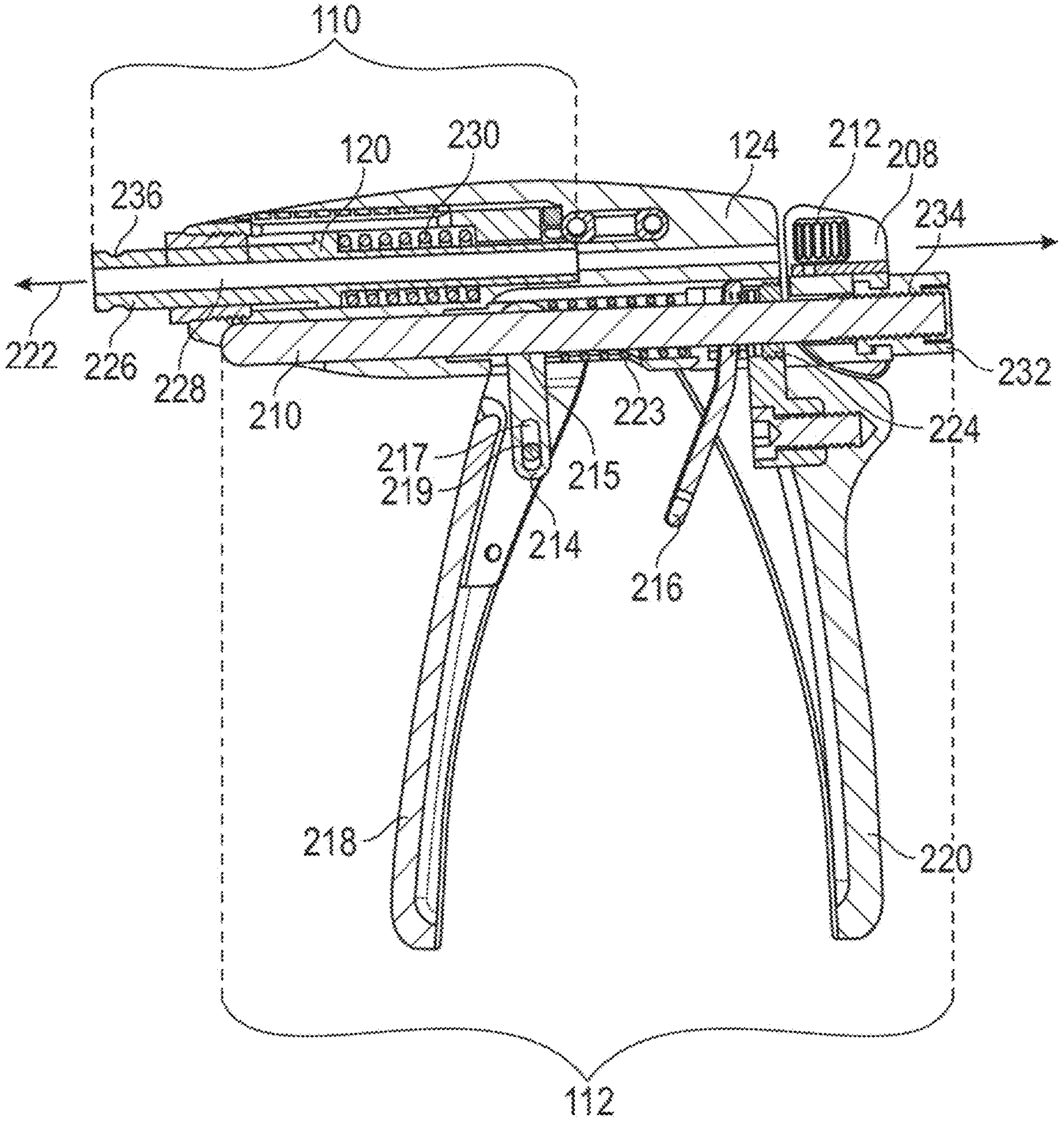
FIG. 2 is a cross-sectional view of one embodiment of a tensioner according to the present disclosure.

One exemplary embodiment of a system 100 according to the present disclosure is illustrated in FIGS. 1-3. The system 100 can comprise a tensioner 102 and a counter tensioner 104, which are used in combination for manipulating implants 106 coupleable by a cord 108. The tensioner 102 is designed to enable one-handed operation to apply tension to a cord 108. The tensioner 102 can comprise a nose assembly 110 for receiving the cord 108 and a cord lock assembly 112 for securing and applying tension to the cord 108. The counter tensioner 104 can be releasably coupleable to a head of an implant 106 at a distal end 114 thereof and can have a port 118 disposed in a proximal end 116 thereof. The port 118 can be releasably coupleable the nose assembly 110 of the tensioner 102. The counter tensioner 104 can further be rigidly coupleable to both the head of the implant 106 and the nose assembly 110, allowing a surgeon to tension the cord 108 via the tensioner 102 and translate the implant 106 and underlying vertebrae relative to another implant implanted in an adjacent or nearby vertebrae via a handle 130 in the same surgical step and as explained in greater detail below.

The implant 106 can be, for example and without limitation, a threaded fastener, a bone screw, a pedicle screw, a staple, a bone clamp, a universal bone clamp, cam blocks, bone plates, and the like. Furthermore, it is contemplated that the tensioner can be used to tension a cord between bones, clamps, or any implant secured to a bone in any manner. The implant 106 can comprise a shaft that purchases underlying bone and a head including features for securely engaging an elongate member that, prior to being secured, can be tensioned to apply forces to manipulate the position of adjacent or nearby vertebrae as a juvenile patient experiences growth. The cord can be, for example and without limitation, any elongate member including a cord, a tether, strap, a cable, a wire, a suture, a thread, or similar flexible ligature. In additional or alternative embodiments, the elongate member can have some beneficial temporal elastic properties that could, for example and without limitation, avoid overcorrection or under correction over the life of an implanted system, and the like. The term "cord" is used throughout the present disclosure, but should be understood to include any elongate member.

One exemplary embodiment of a tensioner 102 according to the present disclosure is illustrated in FIGS. 1-2. The tensioner 102 can comprise a nose assembly 110 and a cord lock assembly 112 for applying tension to the cord 108. The nose assembly 110 and the cord lock assembly 112 can be at least partially disposed in the main body 124 of the tensioner 102

The cord lock assembly 112 can comprise a cord lock housing 208 disposed at a distal end of an elongate shaft 210 and can engage a cord 108 therein. The cord lock housing 208 can comprise, for example and without limitation, a cam cleat 212 or the like for engaging and disengaging the cord 108. The elongate shaft 210 can be operably coupled to a shaft clutch 214 to drive the elongate shaft 210 proximally and a shaft lock 216 that can resist return of the elongate shaft 210 in the distal direction at the end point of an actuation cycle of the tensioner 102. The shaft clutch 214 can extend from a first end to a second end. The first end can have an opening 215 disposed therein for receiving the elongate shaft 210 and the second end has a slot 217 disposed therein that is transverse to a longitudinal axis of the elongate shaft 210. The slot 217 receives a pin 219 extending from a front handle 218. Actuation of the front handle 218 shifts the opening 215 disposed in the first end of the shaft clutch 214 off angle to engage and distally translate the elongate shaft 210 as the front handle 218 is actuated towards a stationary rear handle 220. The front handle 218 can be rotatable about a pivot axis 126 (shown in FIG. 1) that is transverse to a longitudinal axis 222 extending from a proximal end to a distal end of the main body. A shaft spring 223 positioned proximal to the shaft clutch 214 and about the elongate shaft 210 can urge the shaft clutch 214 and front handle 218 back to the starting point of the actuation cycle of the tensioner 102. The shaft lock 216 can be biased via a distally-located lock spring 224 to allow distal translation but not distal translation of the elongate shaft 210. The shaft lock 216 can be released by articulating the shaft lock 216 proximally if the tension on the cord 108 needs to be released, such as once the cord 108 is secured within the implant 106. Additionally or alternatively, a cord nut 232 disposed on proximate a proximal end of the cord lock housing 108 can be rotated to adjust the cord tension via engagement with threading 234 disposed on the proximal end of the elongate shaft 210. In one example, the elongate shaft 210 can be proximally translated from about 30 mm to about 35 mm during each actuation cycle or stroke of the shaft clutch 214. The tensioner 102 can be actuated via a single hand of a surgeon, freeing the other hand for performing other surgical tasks during and adjacent to cord tensioning.

The nose assembly 110 can comprise a piston 226 having a lumen 228 extending therethrough for receiving the cord and a load spring 230 positionable in contact with an indicator region 120 disposed on the piston 226. The indicator region 120 of the piston 226 can have a cross-sectional diameter than can be greater than or equal to any other portion of the piston 226. A nose cap 232 can retain the piston 226 and load spring 230 in the main body 124 of the tensioner 102. The load spring 230 can be calibrated so that the position of the indicator region 120 of the piston 226 correlates to the load applied to the cord as the cord 108 is tensioned and there is a counter pressure applied by the counter tensioner 104 to the nose assembly 110. The indicator region 120 can be visible through a window 122 disposed on the main body 124 of the tensioner 102 having indicia 128 printed adjacent thereto indicative of cord load at various indicator region positions relative to the tensioner main body 124, as best illustrated in FIG. 1. The piston 226 can have a detent 236 disposed in a circumferential outer surface of the piston 226 proximate a distal end thereof for coupling to the counter tensioner 104.

Figure 3A:
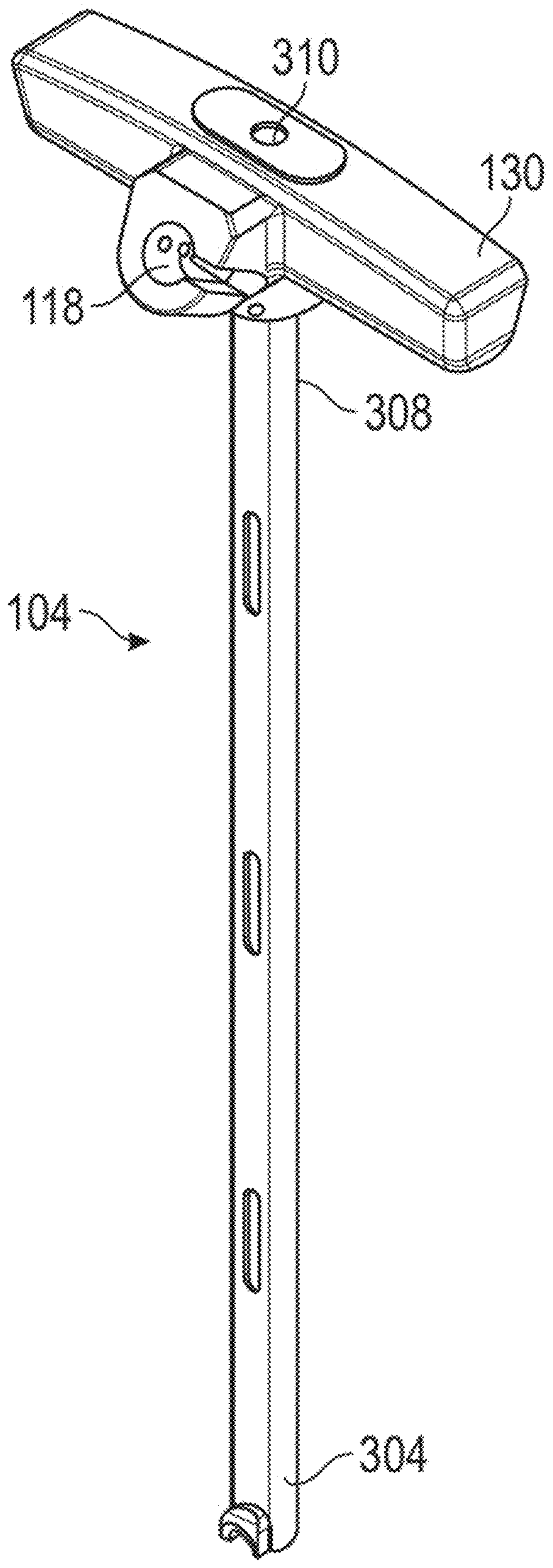
FIG. 3A is a perspective view of an embodiment of a counter tensioner according to the present disclosure and FIG. 3B is an exploded view of the counter tensioner of FIG. 3A.
Figure 3B:
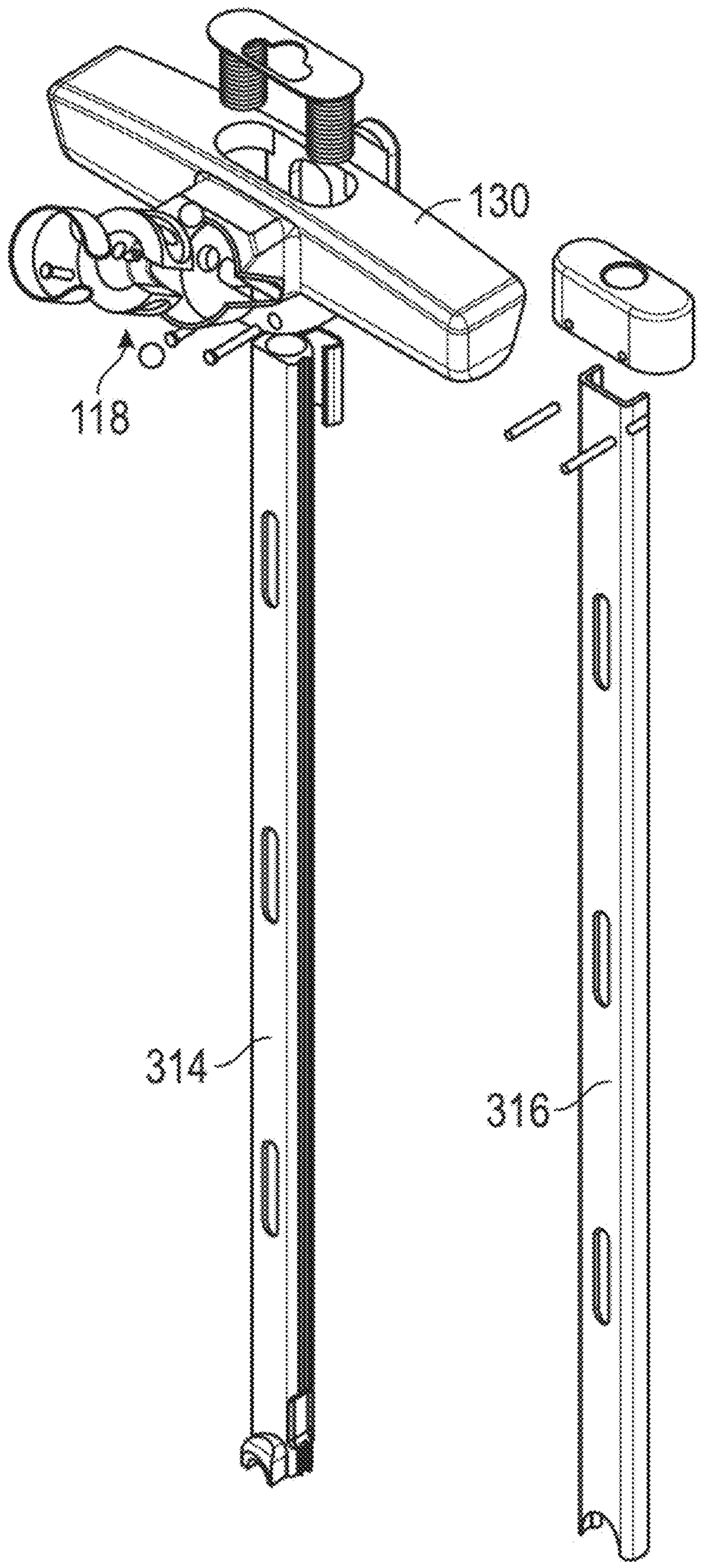
Figure 4A:
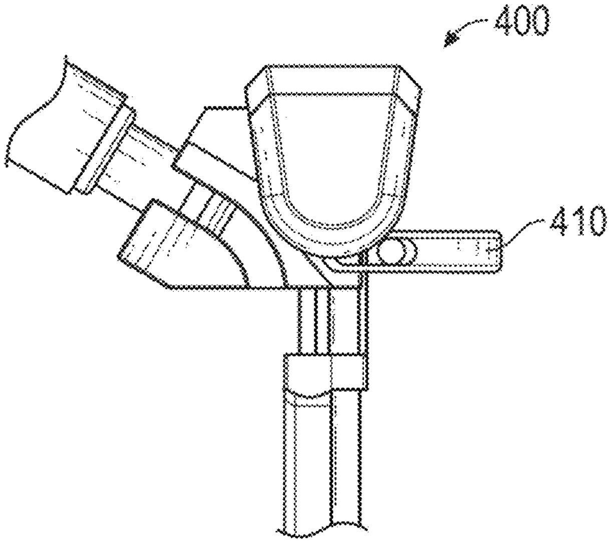
FIG. 4A is a partial perspective view of an embodiment of a proximal end of the system in use in a first position and FIG. 4B is a partial perspective view of the distal end of the embodiment of FIG. 4A in use.
Figure 4B:
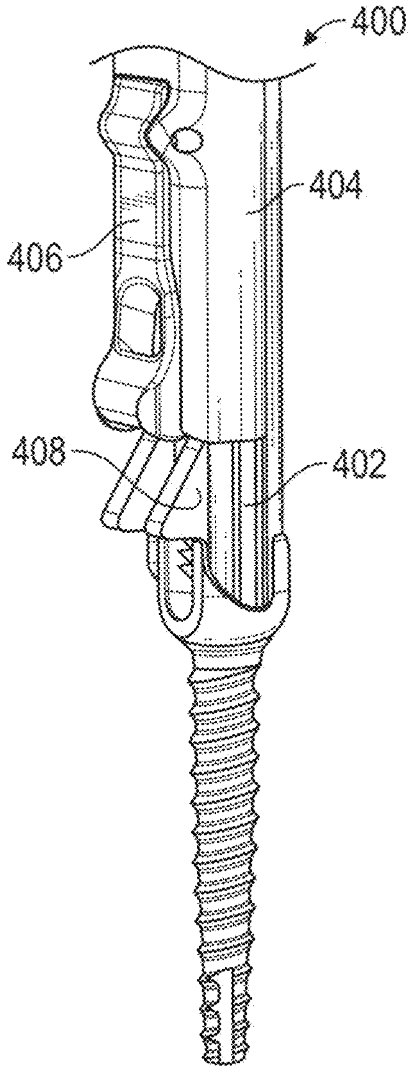
Figure 5A:
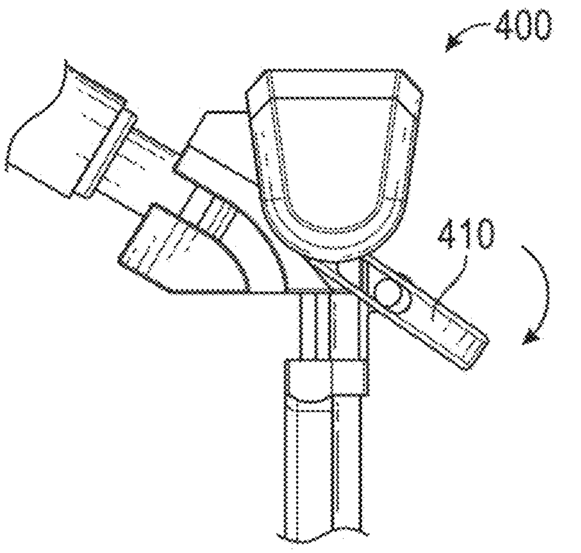
FIG. 5A is a partial perspective view of an embodiment of a proximal end of the system in use in a second position and FIG. 5B is a partial perspective view of the distal end of the embodiment of FIG. 5A in use.
Figure 5B:
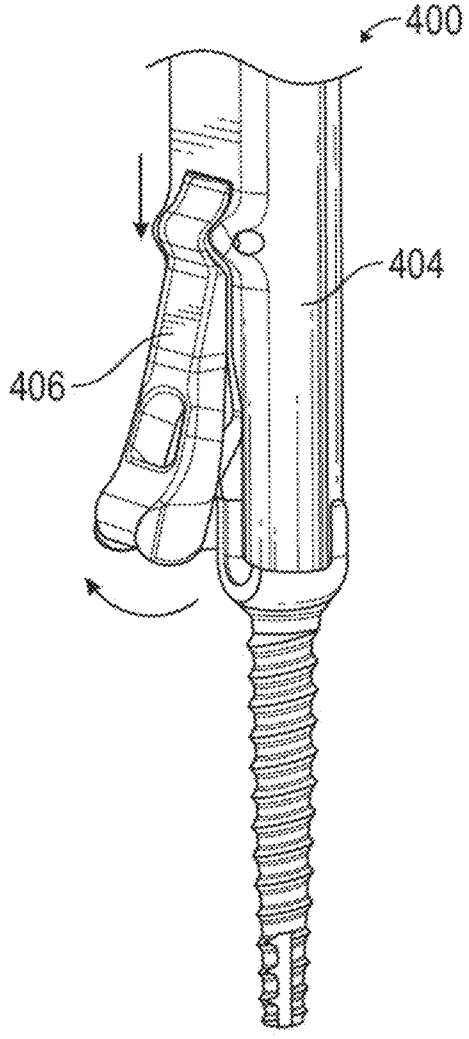

One exemplary embodiment of a counter tensioner 104 according to the present disclosure is illustrated in FIGS. 1, 3A, and 3B. The counter tensioner 104 can be releasably coupleable to the head of an implant 106 at a distal end 304 thereof. The counter tensioner 104 can guide the cord 108 to a port 118 proximate the proximal end 308 thereof. The port 118 can allow the cord to be fed through the nose assembly 110 to be secured in the cord lock housing 206 of the cord lock assembly 112. The port 118 can rigidly, releasably receive the nose assembly 110 of the tensioner 102 via a capture ball disposed in the port 118 for engaging the detent 236 of the piston 226. The counter tensioner 104 can further comprise a lumen 310 disposed therein extending from the distal end 304 to the proximal end 308 thereof. The port 118 can be disposed at an angle that is not parallel to a longitudinal axis of the lumen 310. A set screw (not shown) can be deliverable through the lumen 310 and engageable with the head of the implant to secure the cord therein with a driver (not shown). The counter tensioner 104 can comprise a handle 130 that can facilitate translation of the implant 106 relative to another implant implanted in an adjacent or nearby vertebrae. Accordingly, vertebral translation, cord tensioning, and cord fixation can be performed in the same surgical step.

The counter tensioner 104 can further comprise an inner sleeve 314 and an outer sleeve 316. The inner sleeve 314 can comprise a plurality of outwardly biased arms at a distal end thereof that are engageable with cooperating features disposed on the head of the implant. Advancing the outer sleeve 316 distally over the inner sleeve 314 and at least partially over the head of the implant can urge the outwardly biased arms into secure engagement with cooperating features on the head of the implant.

Another exemplary embodiment of a counter tensioner 400 according to the present disclosure is illustrated in FIGS. 4A-5B. Here, the counter tensioner 400 can comprise an inner sleeve 402 and an outer sleeve 404. A distal end of the outer sleeve 404 comprises a fulcrum 406 that can move from a first position where the fulcrum 406 is parallel to a longitudinal axis of the counter tensioner 400 to a second position where the fulcrum 406 pivots outwardly from the longitudinal axis of the counter tensioner 400. The inner sleeve 402 can comprise at least one projection 408 that can urge the fulcrum 406 outward as the outer sleeve 404 passes distally over the inner sleeve 402 and at least partially over the head of the implant. The fulcrum 406 serves to change the cord angle, easing local tension on the cord as it is routed up to the tensioner 102 engaged in the port 118. Optionally, a pivoting latch 410 can be provided at a proximal end of the inner sleeve 402. The pivoting latch 410 can be operatively coupled to the counter tensioner 400 so that the pivoting latch 410 moves downward as the fulcrum moves toward a parallel orientation relative to the longitudinal axis of the counter tensioner 400 and upward as the fulcrum pivots outwardly from the longitudinal axis of the counter tensioner. As a skilled artisan will appreciate in light of the present disclosure, the fulcrum can reduce stress applied to the cord during the tensioning process.

Figure 6:
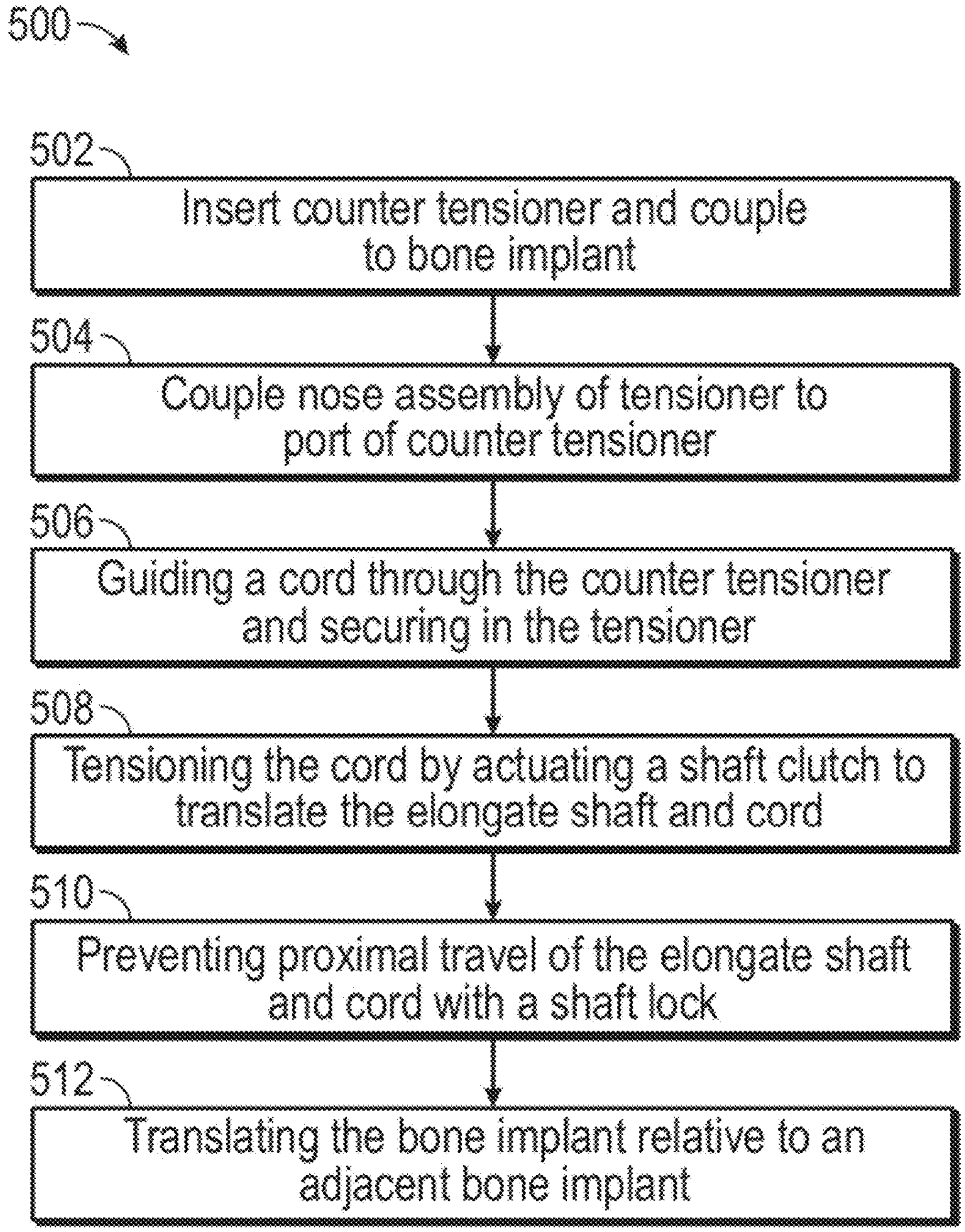
FIG. 6 is a flow chart illustrating steps in one exemplary method according to the present disclosure.

FIG. 6 is a flowchart illustrating a method 500 according to an exemplary embodiment. The method 500 can include operations such as coupling a counter tensioner to an implant at 502; coupling a tensioner to the counter tensioner at 504; routing a cord through the counter tensioner and securing the cord in the tensioner at 506; and tensioning the cord at 508. The method 500 can begin at 502 with a counter tensioner, such as counter tensioner 104, being inserted through an incision and coupled to a head of an implant. In an example, the counter tensioner 104 includes an inner sleeve (e.g., inner sleeve 314) including biased arms located at a distal end thereof and an outer sleeve (e.g., outer sleeve 316). In this example, the biased arms can be engaged with cooperating features on the head of the implant, and the outer sleeve can subsequently be slid distally to lock the biased arms onto the head of the implant. In another example, the counter tensioner can include a threaded feature, a quick connect feature, or the like at a distal end thereof to couple the counter tensioner 104 to complementary features disposed on the head of the implant. In yet another additional or alternative example, the counter tensioner 104 can engage the head of the implant such that the longitudinal axis of the implant and the longitudinal axis of the counter tensioner are not parallel and the cord can couple the counter tensioner to the implant.

At 504, the method 500 can continue with the tensioner 102 being coupled to the counter tensioner 104. In an example, the tensioner 102 includes a nose assembly 110 including a piston 226 formed from a cylinder with a detent 236 disposed in a circumferential outer surface and proximate a distal end thereof. The detent 236 in the piston 226 can engage a capture ball biased into the port 118.

At 506, the method 500 can continue with guiding a cord from the proximal end of the counter tensioner 104, through the port 118 and a lumen 228 disposed in a piston 226 of the nose assembly 110 of the tensioner 102, and securing the cord within a cord lock housing 208 of a cord lock assembly 112 disposed at the end of an elongate shaft 210, the cord being secured in an implant 106 in an adjacent or nearby vertebrae.

At 508, the method 500 can continue with tensioning the cord 108 by actuating a front handle 218 of the tensioner 102 to cause a shaft clutch 214 to engage and distally translate the elongate shaft 210 and the cord 108.

At 510, the method 500 can continue by preventing proximal travel of the elongate shaft 210 at the end of the stroke of the shaft clutch 214 by causing the shaft lock 216 to engage and prevent return of the elongate shaft 210.

At 512, the method 500 can optionally include translating the implant and underlying vertebrae relative to an implant of an adjacent or nearby vertebrae. Here, a surgeon can grasp handle 130 to translate the implant coupled to the counter tensioner 104. The steps of tensioning the cord and translating the vertebrae can be performed simultaneously.

The method can further comprise indicating a load on the cord by the position of an indicator region of a piston of the nose assembly relative to indicia printed adjacent a window in a main body of the tensioner. As the cord is tensioned and counter pressure is applied to the piston of the nose assembly, the piston depressed the load spring and an indicator region of the piston moves in the window disposed in the main body relative to the printed indicia printed adjacent to the window to indicate the load applied to the cord.

Another exemplary embodiment of a cord tensioning system, system 700, is illustrated in FIGS. 7A-7G. The system 700 can comprise a tensioner 702 and a counter tensioner 704, which are used in combination for manipulating implants 106 coupleable by a cord 108 (not illustrated in conjunction with this example). The tensioner 702 is designed to enable one-handed operation to apply tension to a cord 108 (similar to that shown in FIG. 1). The tensioner 702 includes similar structural features to tensioner 102 discussed in reference to FIGS. 1-3, and will not be further described in reference to this example. The counter tensioner 704 can be releasably coupleable to a head of an implant 106 at a distal end 714 thereof and can have a port 718 disposed in a proximal end 716 thereof. The port 718 can releasably receive the nose assembly of the tensioner 702 (tensioner 102 is interchangeable with tensioner 702). The counter tensioner 704 can further be rigidly coupleable to both the head of the implant 106 and the nose assembly, allowing a surgeon to tension the cord 108 via the tensioner 702 and translate the implant 106 and underlying vertebrae relative to another implant implanted in an adjacent or nearby vertebrae via a handle 730 in the same surgical step and as explained in greater detail below. The remaining discussion of counter tensioner 704 focuses on the aspects that differ from examples discussed above.

In this example, the counter tensioner 704 includes a handle 730 with additional features, such as a lock position 732, an unlock position 734, and a lock handle 736. The lock handle 736 is rotatable between the lock position 732 and the unlock position 734. In the unlock position 734, the counter tensioner 704 can be inserted over an implant, such as implant 106 (e.g., a pedicle screw). Once inserted over the pedicle screw, the lock handle 736 can be rotated into the lock position 732 and elements discussed below will lock the counter tensioner 704 to the pedicle screw. Internal workings of the lock mechanism are discussed in reference to FIGS. 7F and 7G below.

Figure 7A:
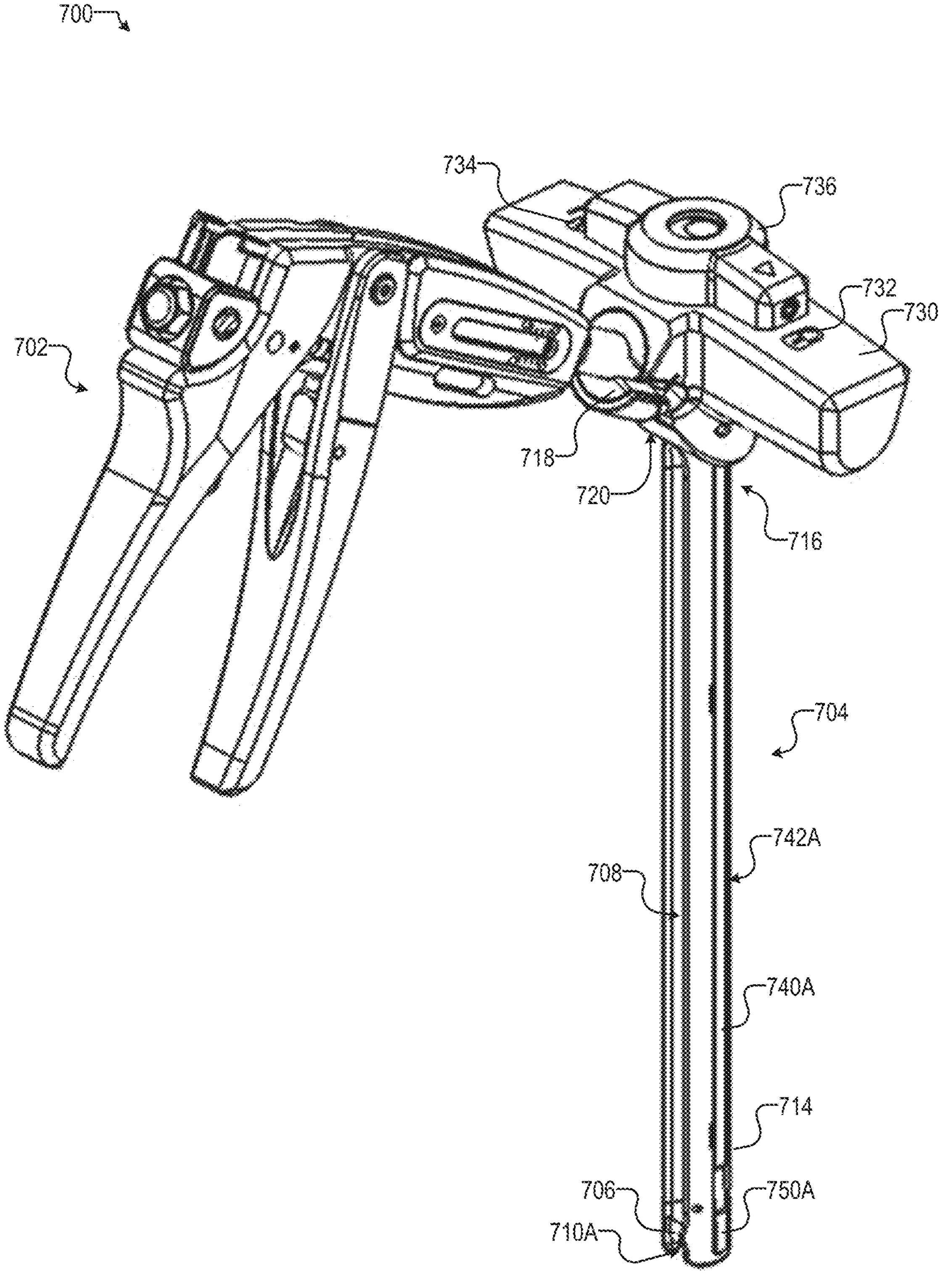
FIGS. 7A-7G illustrate a cord tensioning system, according to various embodiments of the present disclosure.
Figure 7B:
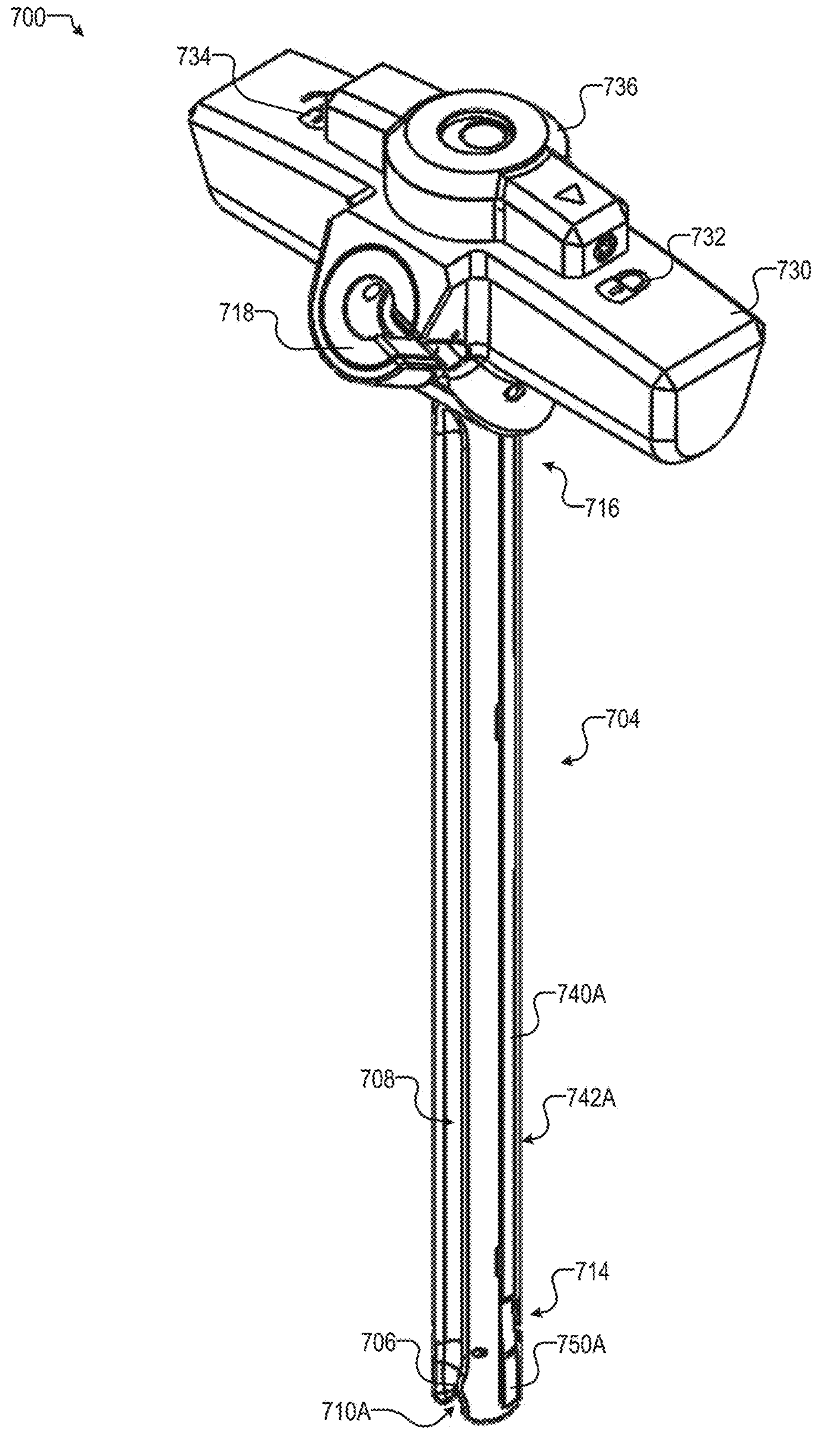

Along the length of the counter tensioner 704 extend a pair of locking extensions 740A, 740B within a pair of locking extension channels 742A, 742B. FIGS. 7A-7B only illustrate locking extension 740A and locking extension channel 742A. In this example, the locking extensions 740A, 740B are square elongate members connected at a proximal end to a locking mechanism operated by the lock handle 736. In other examples, the locking extensions 740A, 740B can be cylindrical rods or other cross-sectional profiles. The locking extension channels in this example are open square (or rectangular) channels, designed to fit the locking extensions 740A, 740B. Moving to the distal end 714 of the counter tensioner 704, the locking extension 740A engages one of the pivot locks 750A (pivot lock 750B is disposed on the opposite side, and shown in FIGS. 7D and 7E). In other examples, the locking extension channels can be a different cross sectional shape and/or be internal to the counter tensioner 704. FIGS. 7A and 7B also illustrate a cord fulcrum 706, a cord channel 708, and a cord guide 710A (cord guide 710B is an opening on the opposing side of the distal end 714 not illustrated in this example). The cord guide 710A allows the cord to exit the counter tensioner 704 and pedicle screw. The cord guides 710A, 710B are designed to complement the U-shaped pedicle screw head adapted to receive the cord. The cord fulcrum 706 includes an enlarged radius area to smooth directional change in the cord from a first direction essentially transverse to a longitudinal axis of the counter tensioner 704 to a second direction essentially parallel the longitudinal axis (see FIG. 1, the cord fulcrum 706 operates in a manner similar to fulcrum 106). In contrast to fulcrum 106, the cord fulcrum 706 is an integral part of the distal end 714, and does not include any moving parts (e.g., does not pivot). From the cord fulcrum 706, the cord extents proximally along the cord channel 708 until entering the cord conduit 720 at the base of the tensioner port 718, which is more clearly illustrated in FIG. 7G. The cord channel 708, in this example, is a semi-circular recess in the elongate portion of the counter tensioner 704.

Figure 7C:
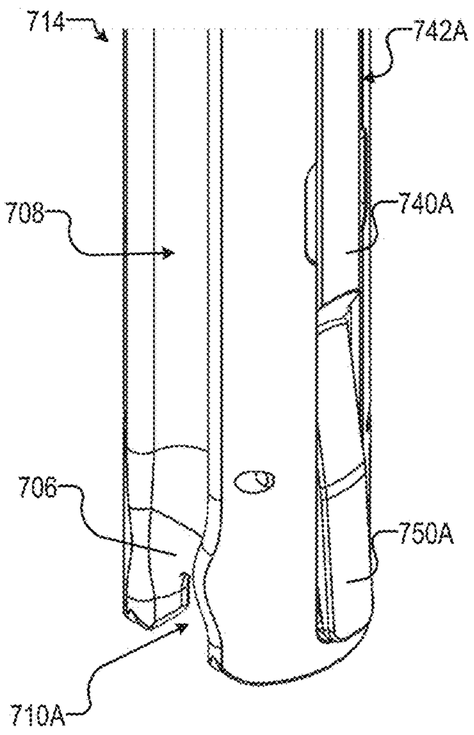

FIG. 7C is a close-up perspective view of the distal end 714 of the counter tensioner 704. A number of the structures discussed above are shown in additional detail, including the cord fulcrum 706, the cord channel 708, the cord guide 710A, a distal end of the locking extension 740A, the locking extension channel 742A, and the pivot lock 750A. FIG. 7C illustrates the counter tensioner 704 in an unlocked position. The cord fulcrum 706 in particular is shown in greater detail, in this figure it is easier to make out the radius created by the cord fulcrum 706. The enlarged radius provides a smoother transition for the cord coming out of the cord guide 710A and proceeding up along the cord channel 708.

Figure 7D:
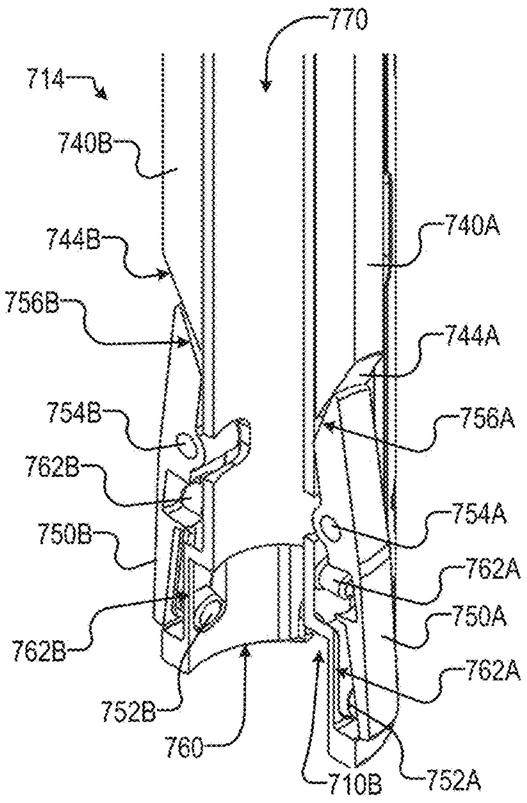
Figure 7E:
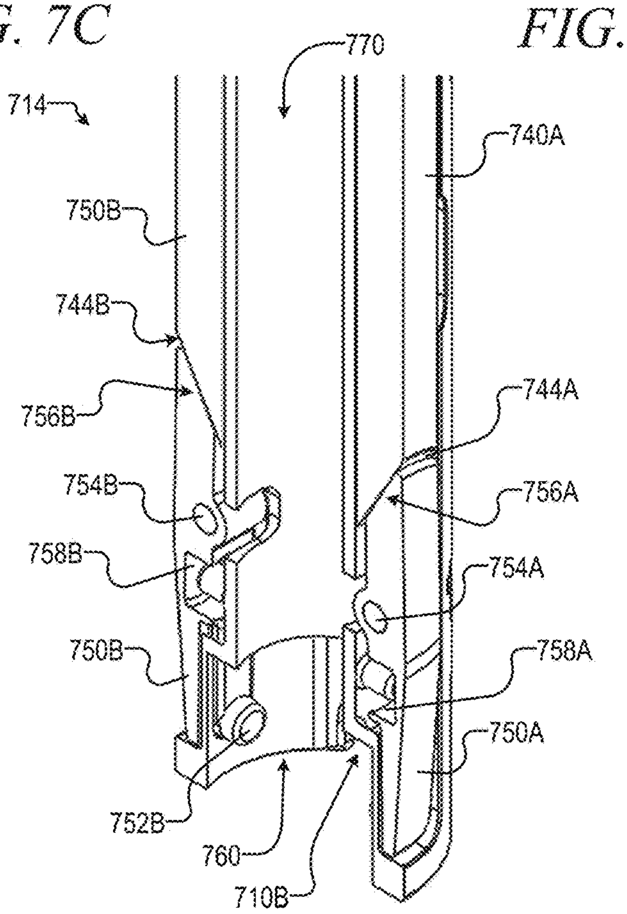

FIGS. 7D and 7E provide cross sectional views of the distal end 714 of the counter tensioner 704 in an unlocked and locked state, respectively. The cross sections provide a detailed view of both sides of the counter tensioner 704. For example, both locking extensions 740A, 740B are shown extending down opposite sides of the counter tensioner 704 and terminating in extension wedges 744A, 744B. The extension wedges 744A, 744B tapper the locking extensions 740A, 704B down to a thin edge along the distal most portion. In this example, the extension wedges 744A, 744B tapper at approximately 60 degrees, but other tappers can be used. The extension wedges 744A, 744B engage with lock wedges 756A, 756B, respectively. The lock wedges 756A, 756B in this example tapper at a corresponding amount to produce an essentially opposing structure to the extension wedges 74A 744B. In some examples, the ramp (tapper) angle on the lock wedges 756A, 756B is slightly greater or slightly less than the extension wedges 756A, 756B to reduce friction between the surfaces. The locking mechanism within the handle 730 operates to linearly translate the locking extensions 740A, 740B from the unlocked position shown in FIG. 7D to a locked position shown in FIG. 7E. Upon translation, the extension wedges 744A, 744B engage the lock wedges 756A, 756B and cause the pivot locks 750A, 750B to rotate about pivots 754A, 754B to shift locking pins 752A, 752B into recesses within a head of the pedicle screw. The pivot locks 750A, 750B are biased into an unlocked position by springs (not shown for clarity) disposed within spring recesses 758A, 758B with the springs held in place by spring pins 764A, 764B. The locking pins 752A, 752B operate to secure the counter tensioner 704 on the pedicle screw head when pivoted into the locked position (FIG. 7E). In this example, the locking pins 752A, 752B are cylindrical posts extending radially inward. In other examples, the locking pins 752A, 752B can be different cross-sectional shapes, such as square or rectangular. The pedicle screw is also surrounded by the pedicle screw receptacle 760 that includes pin openings 762A, 762B to receive the locking pins 752A, 752B, respectively. Pedicle screw receptacle 760 receives the longitudinal bore 770, which extends the length of the counter tensioner 704. The longitudinal bore 770 can allow for insertion of a closure top (e.g., set screw) into the pedicle screw to secure the cord. Finally, FIGS. 7D and 7E illustrate cord guide 710B with opposing cord guide 710A shown in FIG. 7C.

Figure 7F:
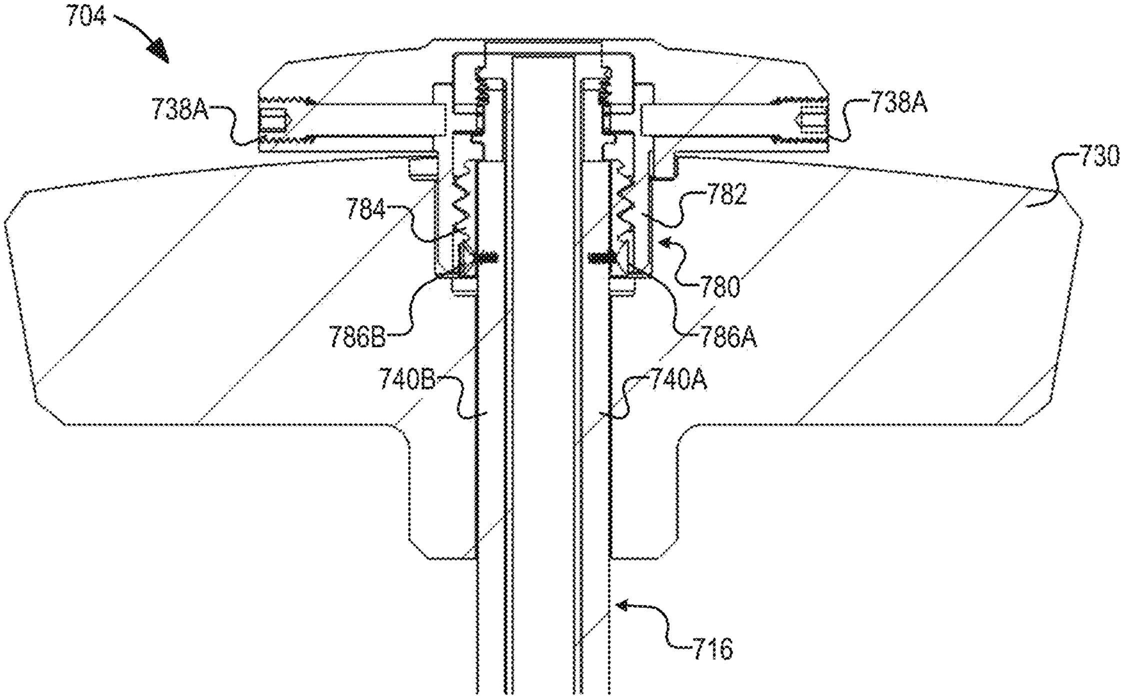
Figure 7G:
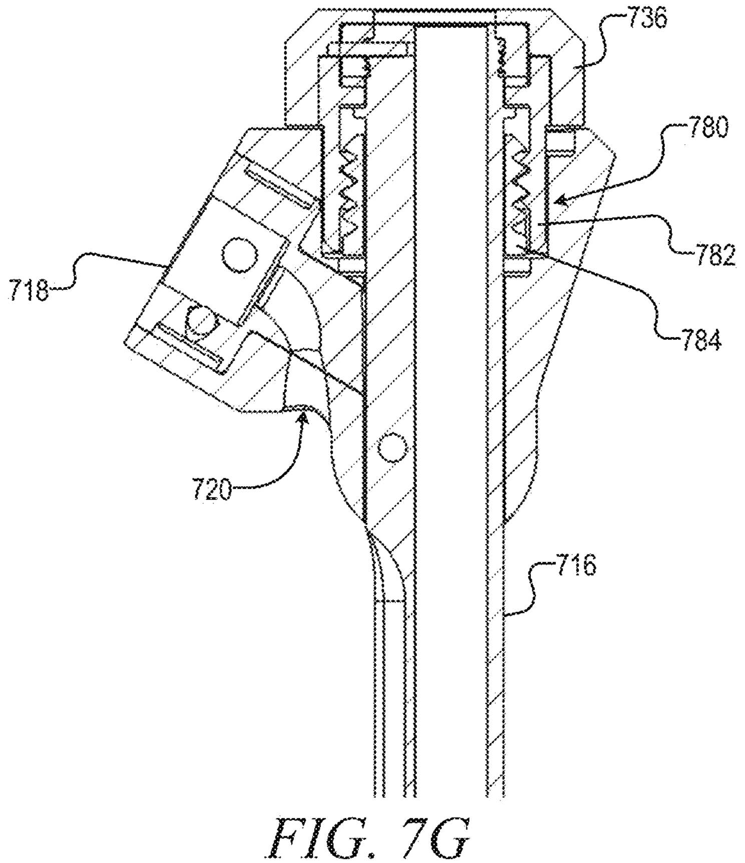

FIGS. 7F and 7G provide cross sectional views of the proximal end 716 of the counter tensioner 704. The cross sectional views include details of the proximal lock mechanism 780 and interaction with the lock handle 736. The proximal lock mechanism 780 operates to linearly translate the locking extensions 740A, 740B, which in turn shift the pivot locks 750A, 750B from an unlocked to locked position as discussed above. The proximal lock mechanism 780 includes a lock cylinder 782 coupled to the lock handle 736 through two lock cylinder set screws 738A, 738B. The lock handle 736 rotates the lock cylinder 782, which in turn causes translation of the locking extension 740A, 740B. The translation is accomplished, in this example, through interaction between a threaded cylinder 784 and a threaded internal portion of the lock cylinder 782. The threaded cylinder 784 is coupled to the locking extensions 740A, 740B through extension coupling pins 786A, 786B. When the lock handle 736 is rotated, the lock cylinder 782 rotates with an internal threaded surface engaging the external threads on the threaded cylinder 784, which is coupled to the locking extensions. As the lock handle 736 and lock cylinder are coupled to the elongate portion of the counter tensioner 704, the threaded interaction causes the threaded cylinder 784 and locking extensions 740A, 740B to translate in a proximal-distal direction. Other mechanisms for translating the locking extensions 740A, 740B can be utilized without deviating from this basic design, such as a cam follower arrangement between the lock cylinder 782 and locking extensions 740A, 740B.

FIG. 7G also provides illustration of the cord conduit 720 leading to the tensioner port 718. As discussed above, the cord can be routed out of the cord guide 710A, around the cord fulcrum 706, proximally along the cord channel 708, through the cord conduit 720, and into the tensioner 702 through the tensioner port 718.

Figure 8A:
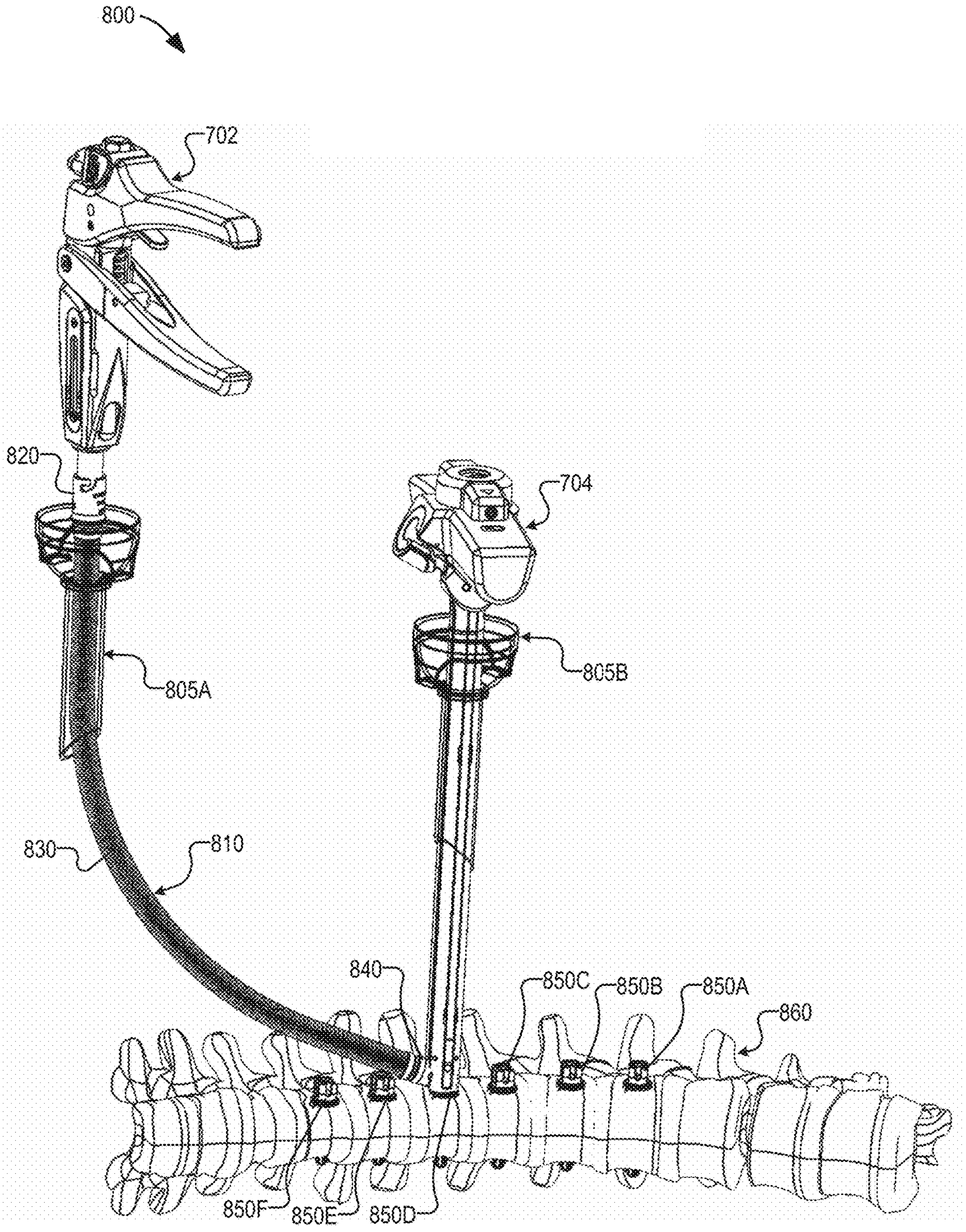
FIG. 8A is a drawing illustrating a cord tensioning system operating through an auxiliary surgical port, according to various embodiments of the present disclosure.

FIG. 8A is a drawing illustrating a cord tensioning system 800 operating through an auxiliary surgical port 805A, according to various embodiments of the present disclosure. In this example, the cord tensioning system 800 is illustrated as including a plurality of surgical ports 805A, 805B (collectively referenced as surgical port(s) 805), a tensioner 702, a counter tensioner 704, and a tensioner extension 810. The cord tensioning system 800 is illustrated in reference to an exemplary spine 860 with spinal implants 850A-850F (collectively or individually referenced as spinal implant(s) 850). In this example, the spinal implants 850 are pedicle screws with tulip heads adapted to receive a surgical cord (not illustrated). The example illustrated in FIG. 8A is intended to demonstrate, generally, how the cord tensioning system 800 is utilized in reference to a patient's spine. However, the illustration is not necessarily to scale or anatomically correct, rather it is merely intended to demonstration how the instruments function in combination and relative relationship.

In general, the cord tensioning system 800 is designed to reduce complexity and increase the speed of implanting a surgical cord (e.g., flexible elongate tether) along a deformed portion of a patient's spine. Prior to creation of the cord tensioning system 800 by the present inventors, implanting a surgical cord involved complex manipulations of the surgical cord through several surgical ports positions directly over the spinal deformity (one or more ports, usually one for every 1 to 3 vertebrae), such as surgical port 805B. The cord manipulations involved securing the cord to a pedicle screw, maneuvering it through the body towards the next pedicle screw, bring the cord up through the surgical port, tensioning the cord, securing the cord to the present pedicle screw, pushing the cord back down through the surgical port and repeating for the next screw. The surgical ports are necessary during this procedure to keep $CO_2$ used to deflate the lung within the body cavity. Manipulating the cord in and out of the surgical ports is a time consuming and challenging part of the surgical procedure.

Utilizing the tensioner extension 810 in combination with an auxiliary surgical port, such as surgical port 805A, positioned inferior to the spinal deformity, can avoid maneuvering the surgical cord into and out of a surgical port for each and every spinal implant. In the revised procedure (detailed further in reference to FIG. 12 below), a surgeon threads the surgical cord through the tensioner extension and utilizes the extension to position the surgical cord into each spinal implant and also tension the cord between spinal implants. The revised procedure avoids the need to thread the cord in and out of a surgical port for each and every spinal implant in the deformity correction construct.

In this example, the tensioner extension 810 can include a dual coupler 820 attached to a proximal end of an elongate extension member 830, as well as a nose member 840 attached to a distal end of the elongate extension member 830. As illustrated, one of the functions of the dual coupler 820 is to enable the tensioner 702 to couple to the tensioner extension 810. As discussed below, the dual coupler 820 is also designed to enable connection of a secondary extension to elongate the core tensioning system 800, which allows for the system to operate over a larger deformity construct with minimal additional steps in the surgical procedure. The tensioner extension 810 can be in the range of 300 mm to 400 mm in length. However, tensioner extensions of different lengths can easily be produced in accordance with this disclosure.

Figure 8B:
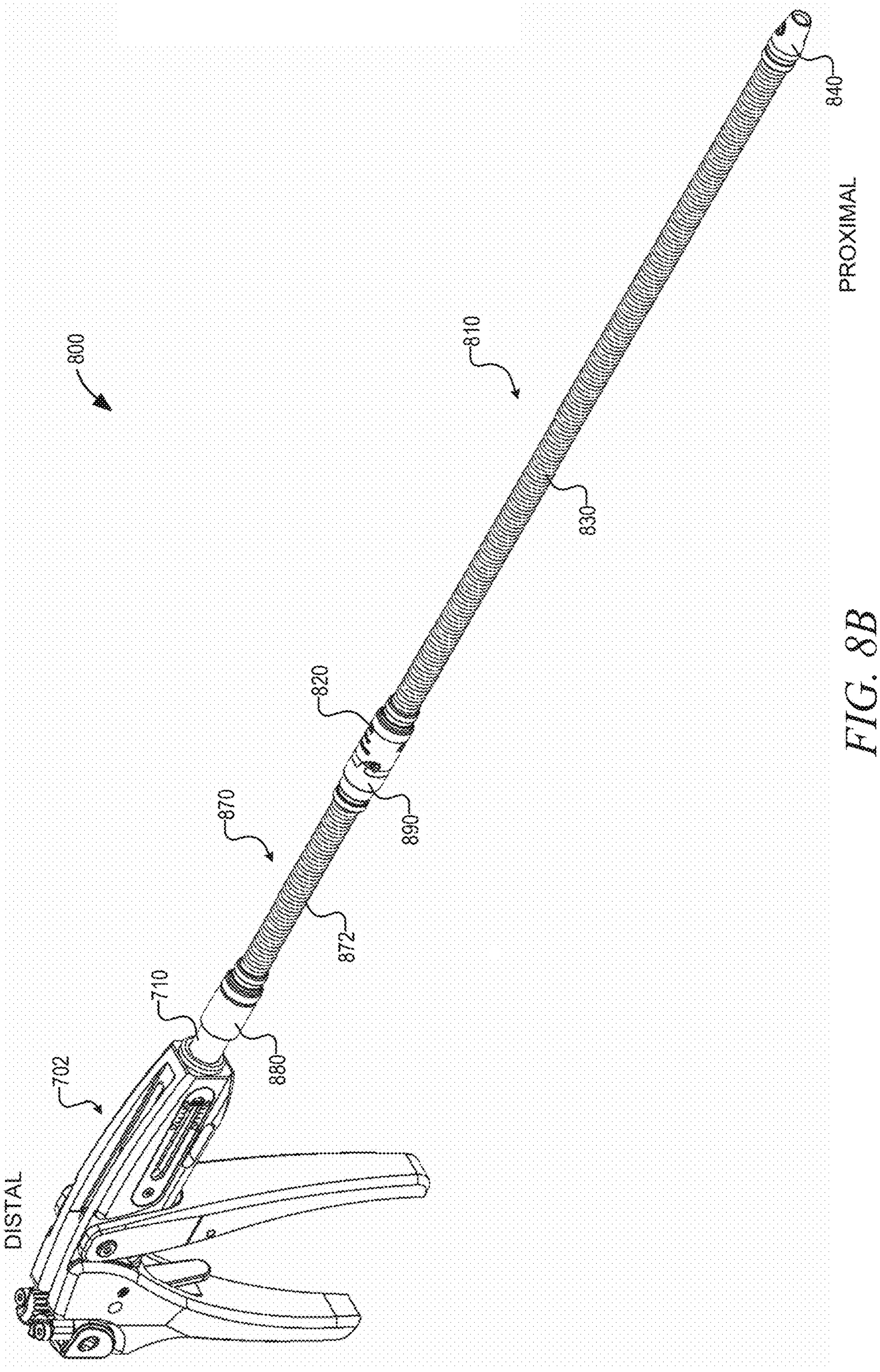
FIG. 8B is a drawing illustrating a cord tensioning instrument including a tensioner extension and secondary extension, according to various embodiments of the present disclosure.

FIG. 8B is a drawing illustrating a cord tensioning instrument 800 including a tensioner extension 810 and secondary extension 870, according to various embodiments of the present disclosure. In this example, the cord tensioning instrument 800 is illustrated with the optional secondary extension 870 coupled between the tensioner 702 and the tensioner extension 810. The secondary extension 870 can provide a surgeon with extra length to reach the most superior spinal implant needed to correct the spinal deformity. The secondary extension 870 is designed to allow for quick connection and disconnection, so that as the surgeon moves closer to the auxiliary surgical port, the overall length of the cord tensioning instrument 800 can be reduced by removing the secondary extension 870 from between the tensioner 702 and tensioner extension 810. Addition or removal of the secondary extension 870 can be performed without re-threading the surgical cord through the tensioner extension 810, which means using it or removing it will not slow down the overall procedure in any significant way.

As illustrated in FIG. 8B, the dual coupler 820 on the tension extension 810 includes structures to enable secure coupling of the secondary extension 870. In this example, the dual coupler 820 can receive the distal extension coupler 890 on the distal end of the short elongate extension member 872 portion of the secondary extension 870. The secondary extension 870 can also include a proximal tensioner coupler 880 affixed to a proximal end of the short elongate extension member 872. In this example, the proximal tensioner coupler 880 includes similar structures as the dual coupler 820 for receiving and securing the nose portion 710 of the tensioner 702. In this example, the short elongate extension member 872 can be a flexible elongate member similar in construction to the elongate extension member 830, but a shorter length. In this example, the secondary extension 870 is in a range of 130 mm to 150 mm in length. As noted above, the elongate members can be a coil spring or silicone tube material, among other materials.

Figure 9A:
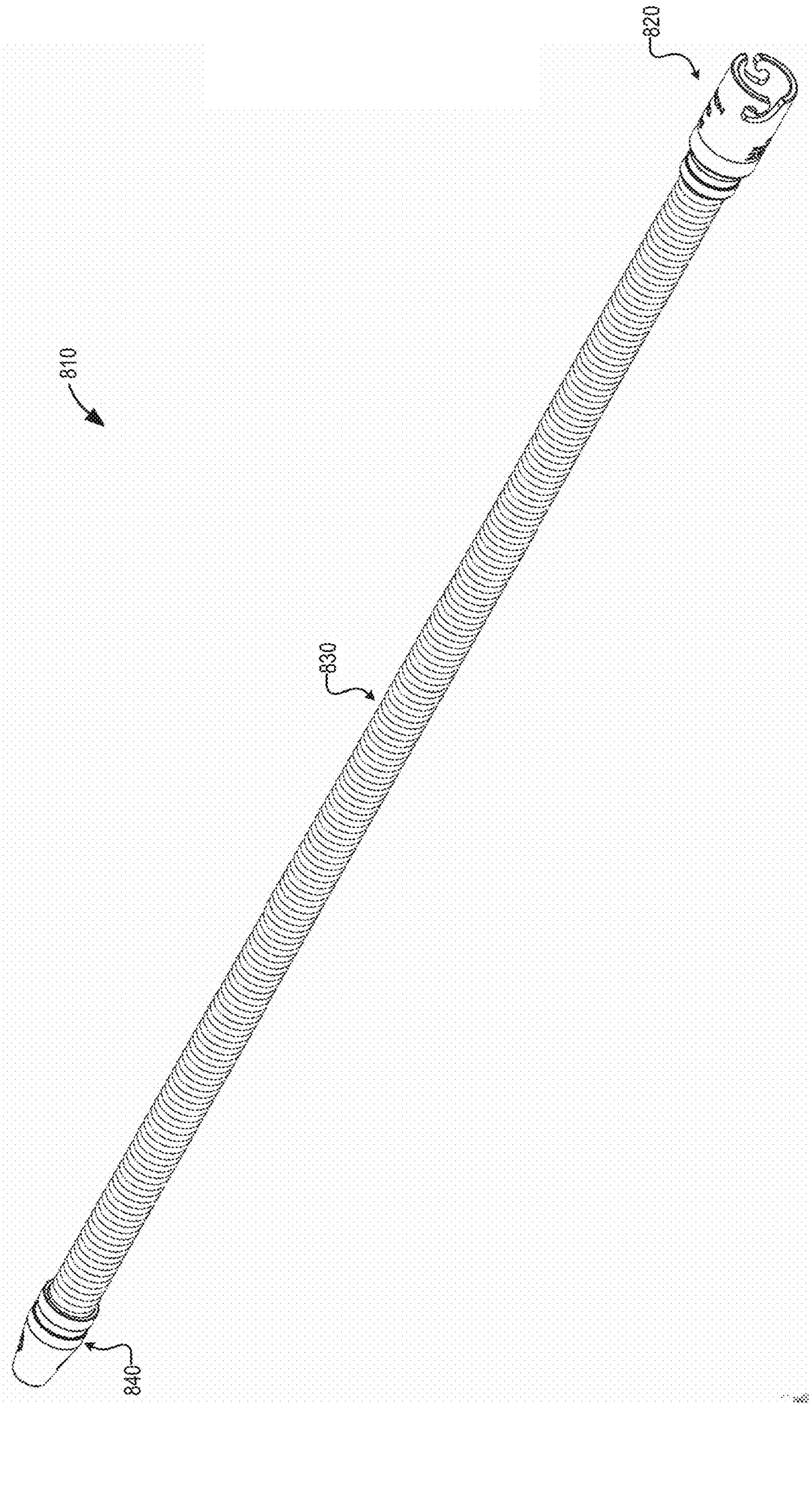
FIGS. 9A-9E are drawings illustrating various aspects of a tensioner extension, according to various embodiments of the present disclosure.
Figure 9B:
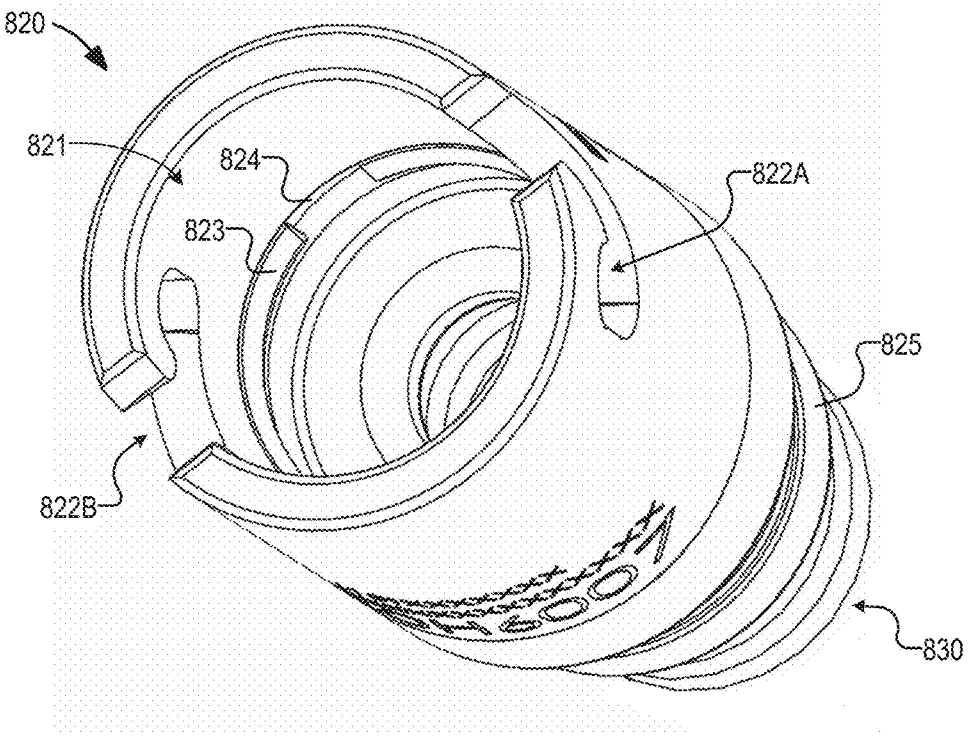

FIGS. 9A-9E are drawings illustrating various aspects of a tensioner extension 810, according to various embodiments of the present disclosure. The following describes the structural components of the tensioner extension 810 in accordance with the example illustrated in FIGS. 9A-9E together. In this example, the tensioner extension 810 includes an elongate extension member 830 between a dual coupler 820 on a proximal end and a distal nose member 840 on the distal end. The illustrated example depicts the elongate extension member 830 as a coil spring with no spacing along the longitudinal length between coils of the coil spring, which allows the construct flexibility and the ability to carry tension along the length of the device. FIG. 9B illustrates a perspective view of the dual coupler 820. In this view, structures such as a coupler bore 821, locking slots 822A, 822B (collectively referenced as locking slot(s) 822), a snap ring 823, a ring groove 824, and a compression member 825. The coupler bore 821 is adapted to receive a nose assembly 710 of the tensioner 702 or a coupler barrel 875 of the secondary extension 870 when the secondary extension 870 is in use. Within the coupler bore 821 is a ring groove 824 with a snap ring 823 disposed within a portion of the ring groove 824. The ring groove 824 is a recess extending around an inner circumference of the coupler bore 821. The snap ring 823 is partially recessed within the ring groove 824, with a rounded or crowned (opposing angles meeting at a raised ridge) surface extending radially into the coupler bore 821. The snap ring 823 only extends partially around the circumference of the ring groove 824, which allows the snap ring 823 to elastically deform. Deformation of the snap ring 823 allows the nose assembly 710 of the tensioner 702 to extend pass the snap ring 823. In some examples, the nose assembly 710 includes a depression or recess extending around the outer circumference that is captured by the snap ring 823 upon insertion into the coupler bore 821.

In this example, the dual coupler 820 includes two opposing locking slots 822. The locking slots 822 each include an opening along the outer edge of the dual coupler 820. From the opening, each locking slot includes a P-shaped cut-out extending along a sidewall of the dual coupler 820 (angling around a small portion of the sidewall). The P-shaped cut-out is shaped to receive a locking pin extending from a coupler portion of the secondary extension 870 (illustrated in FIGS. 10A-10F). The locking slots 822 operate in conjunction with the locking pins to enable a twist-lock coupling between the tensioner extension 810 and the secondary extension 870. The twist-lock operation and structure of the locking slots 822 ensures that the secondary extension remains securely attached to the tensioner extension 810 during use, but also enables quick disconnection when desired.

Figure 9C:
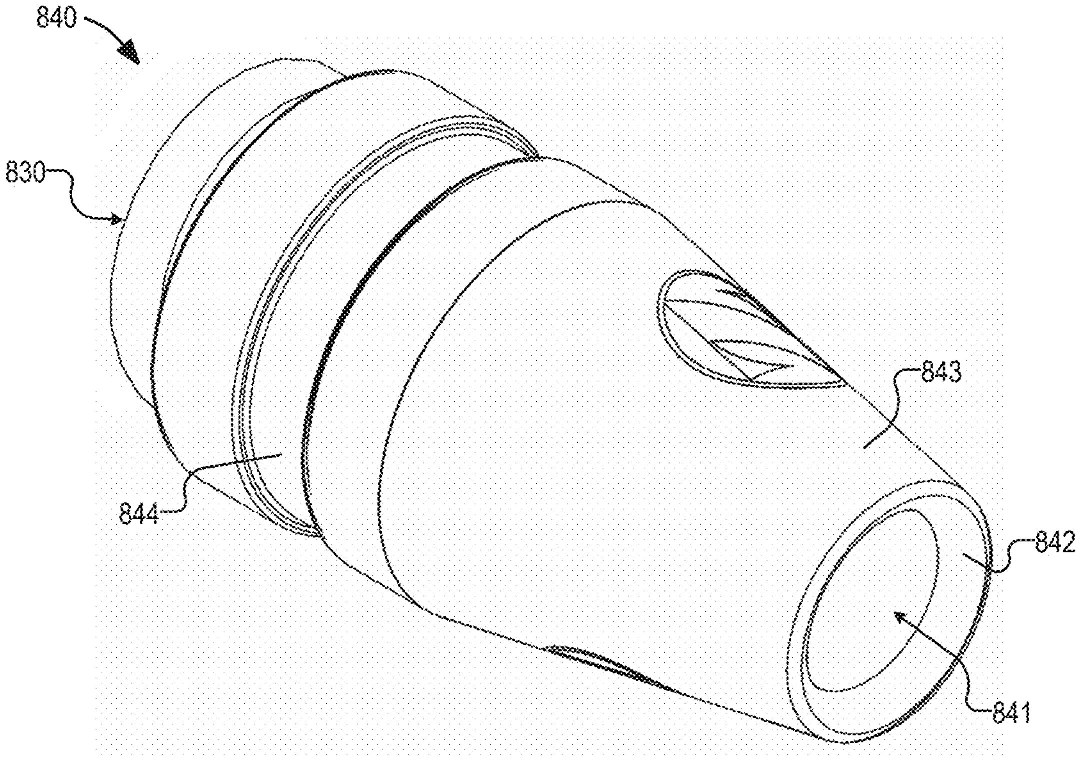

FIG. 9C is a perspective view of an example distal nose member 840. In this example, the distal nose member 840 includes structures such as a nose bore 841, a nose chaffer 842, a tapered body section 843, and a nose compression member 844. The nose bore 841 extends from the distal most end through to a lumen extending the length of the elongate extension member 830. Around the outer edge of the nose bore 841 is a nose chaffer 842, which operates to reduce any friction or wear on the surgical cord exiting the tensioner extension 810. The tapered body section 843 extends proximally away from the distal end ramping up to the transition into the nose compression member 844 that couples the distal nose member 840 to the elongate extension member 830.

Figure 9D:
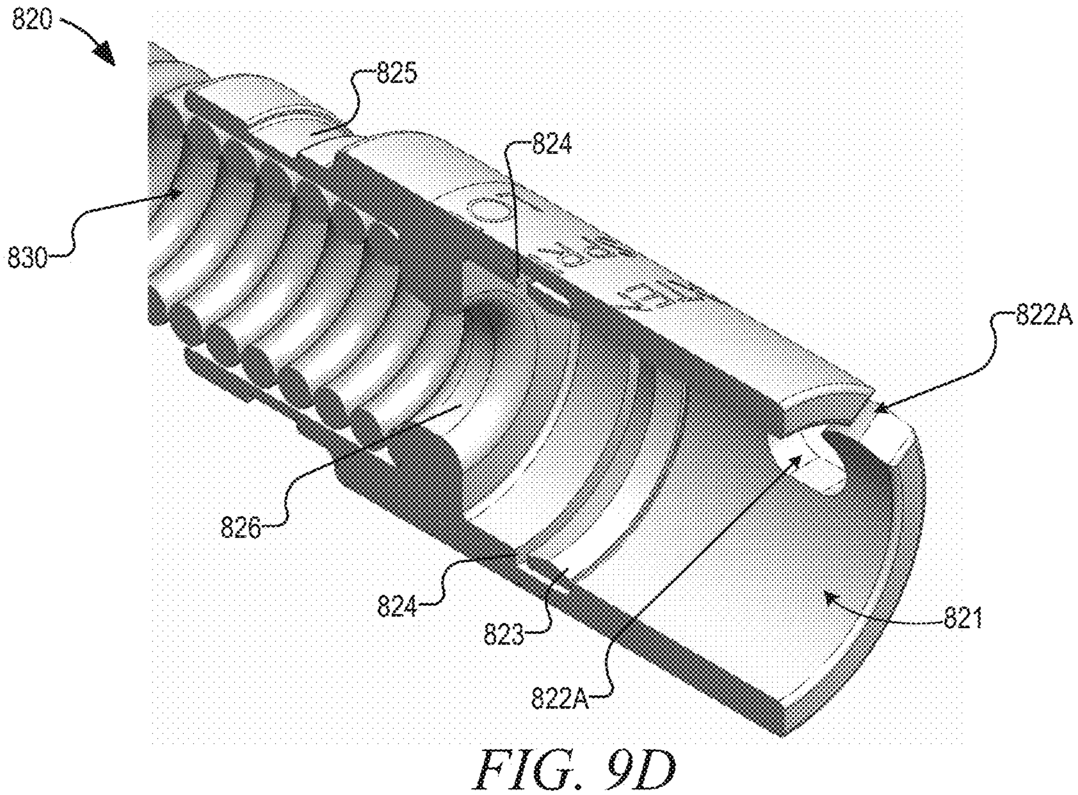

FIG. 9D is a cross-sectional view of the dual coupler 820 connected to the elongate extension member 830. The cross-sectional view provides a more detailed view of the snap ring 823 and ring groove 824, as well as a cord guide 826. The cord guide 826 operates to guide the surgical cord smoothly from the tensioner 702 into the elongate extension member 830.

Figure 9E:
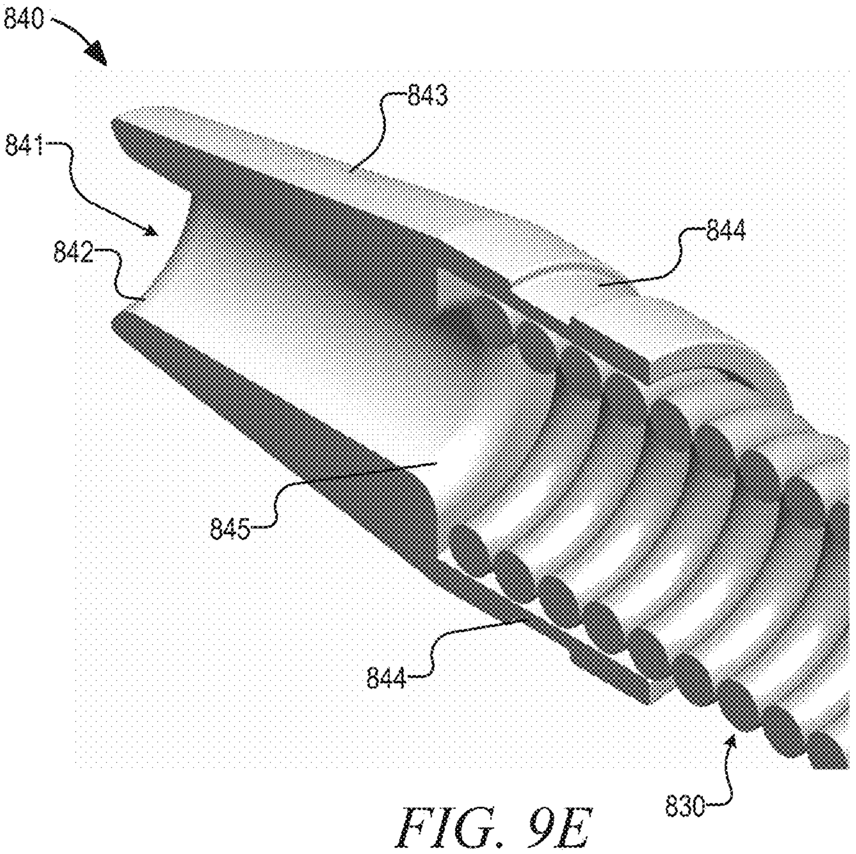

FIG. 9E is a cross-sectional view of the distal nose member 840 connected to the elongate extension member 830. The cross-sectional view details the nose bore 841, the nose chaffer 842, and a nose cord guide 845. The nose cord guide 845 assists in transitioning the surgical cord out of the elongate extension member 830 into the distal nose member 840.

FIGS. 10A-10F are drawings illustrating various aspects of the secondary tensioner extension 870, according to various embodiments of the present disclosure. In this example, the secondary tensioner extension 870 (also referenced simply as the secondary extension 870) includes a secondary extension tensioner coupler 871 coupled to a proximal end of a short elongate extension member 872 as well as an extension coupler 873 capping a distal end of the short elongate extension member 872. The tension coupler 871 includes a snap ring and ring groove comparable to those discussed above in reference to dual coupler 820 for securing the nose assembly 710 of the tensioner 702 (see FIGS. 10D and 10E).

Figure 10A:
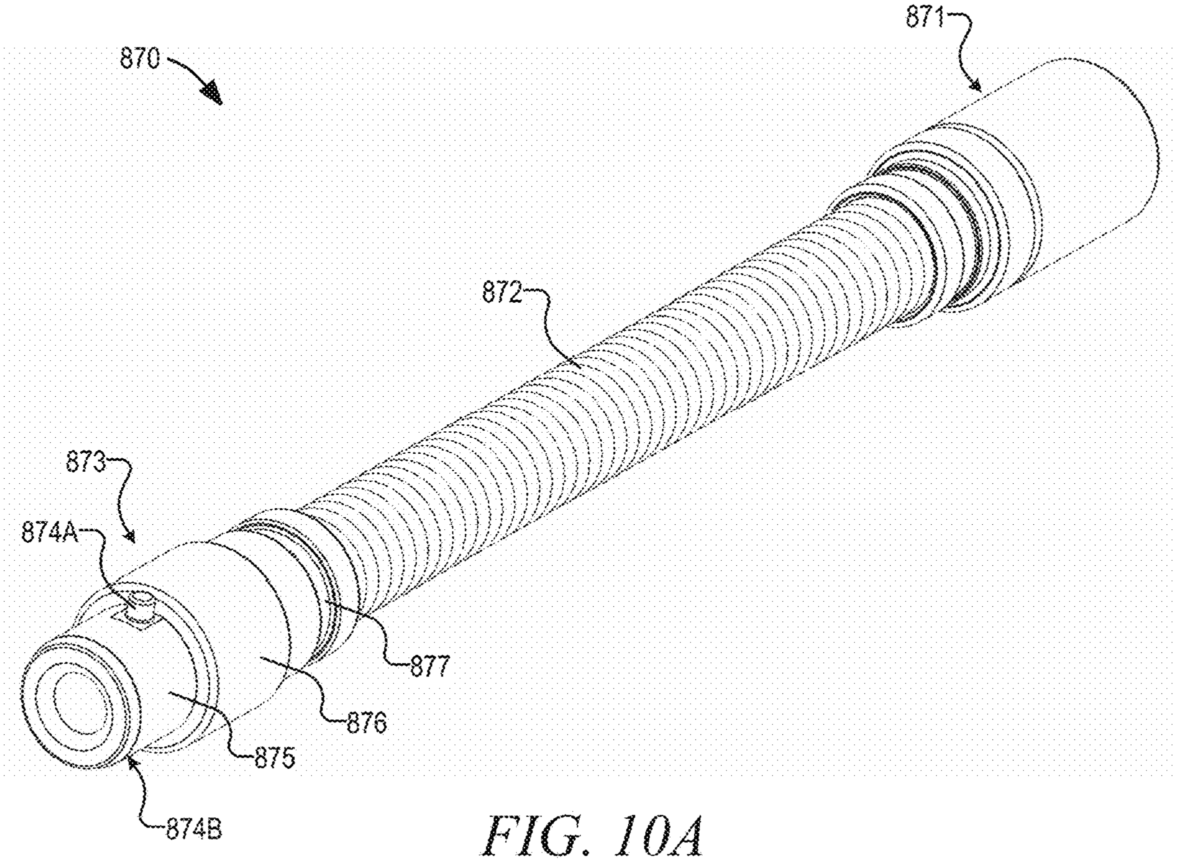
FIGS. 10A-10F are drawings illustrating various aspects of a secondary tensioner extension, according to various embodiments of the present disclosure.
Figure 10B:
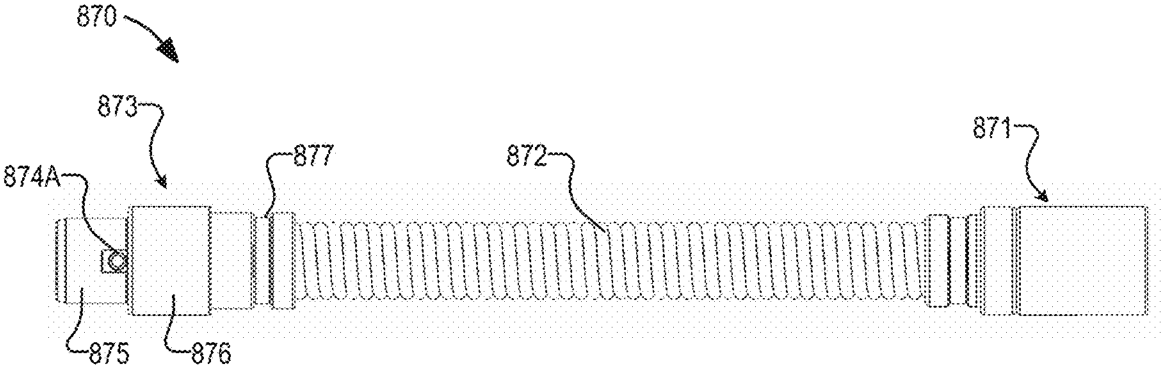
Figure 10C:
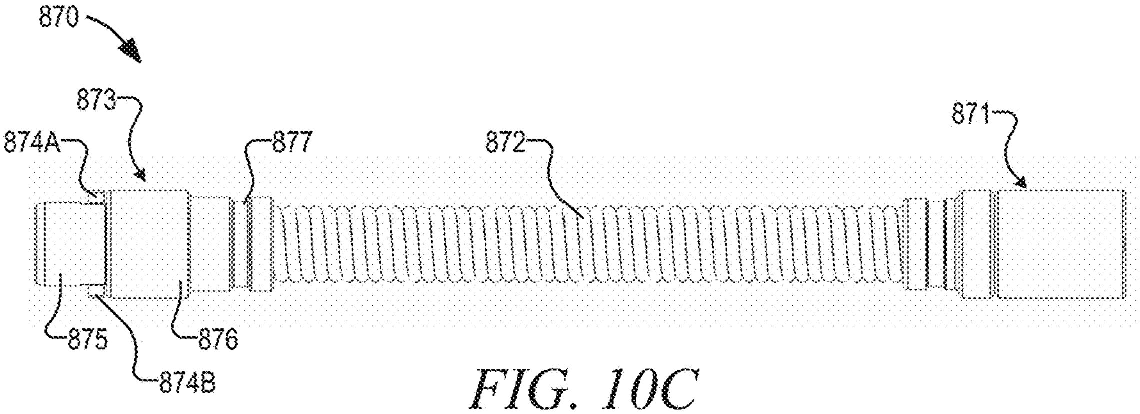
Figure 10D:
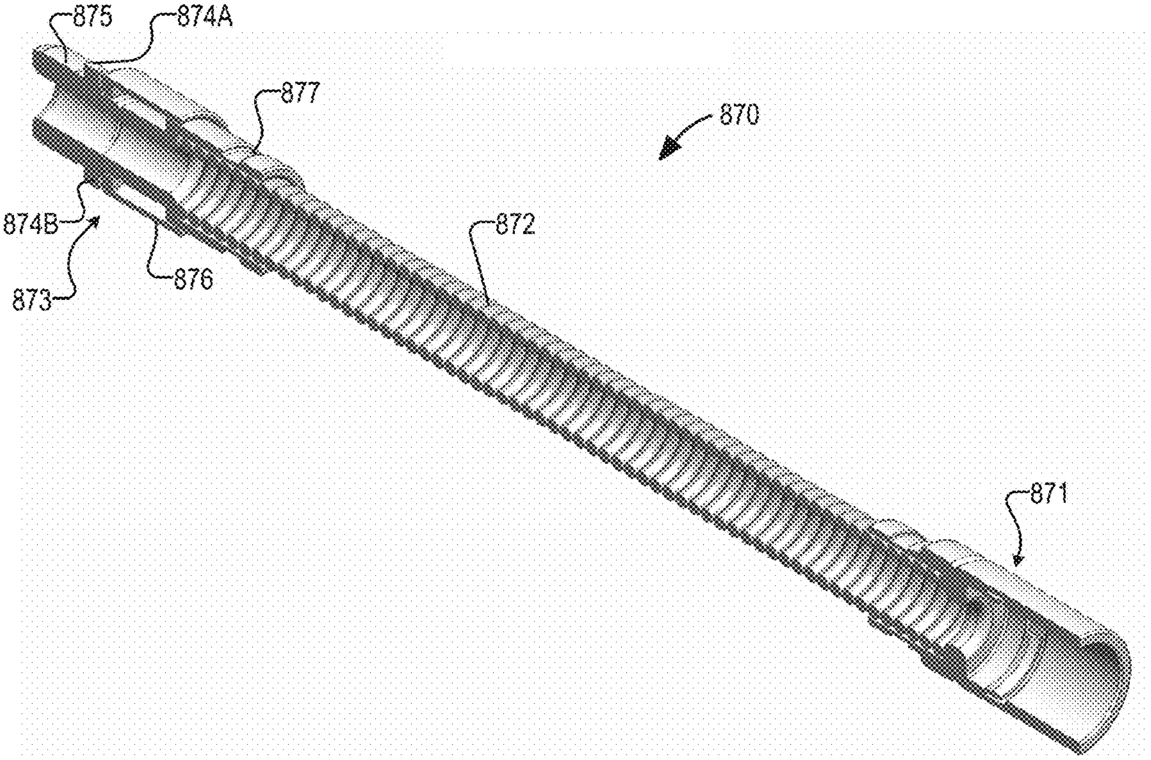
Figure 10E:
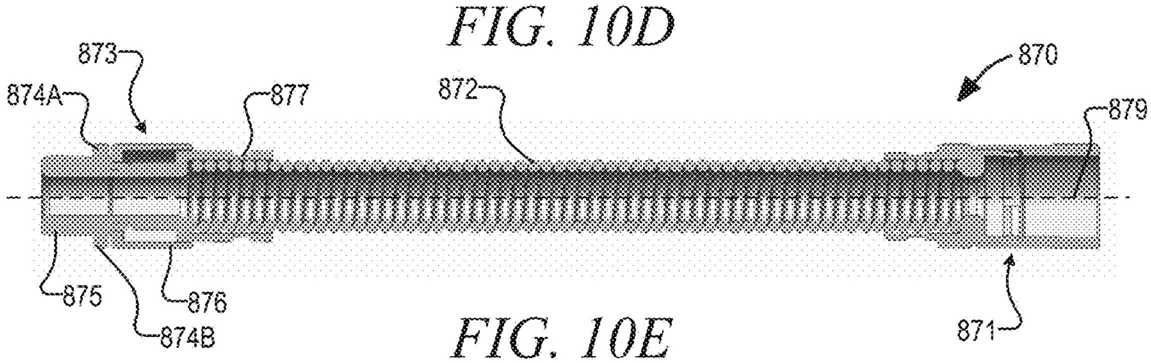
Figure 10F:
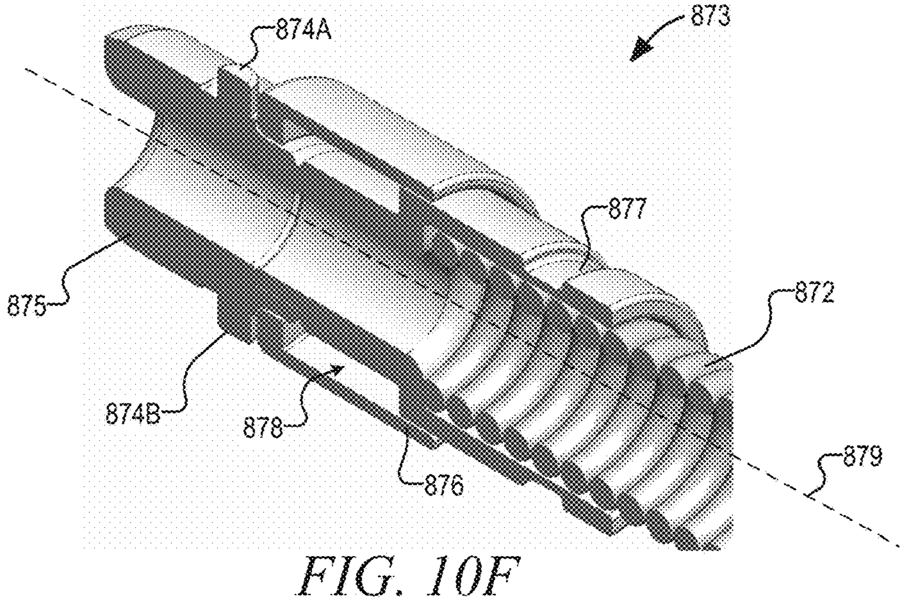

The secondary extension 870 includes extension coupler 873 for securely connecting the secondary extension 871 to the tensioner extension 810. The extension coupler 873 includes locking pins 874A and 874B (collectively referenced as locking pins 874) extending radially away from a coupler barrel 875. As discussed above, the locking pins 874A, 874B interact with locking slots 822 to enable a twist-lock operate to secure the secondary extension 870 to the tensioner extension 810. The locking mechanism can also include a bias cylinder 876, which can be spring loaded or otherwise biased towards the locking pins 874 to assist in securing the secondary extension 870. A spring recces 878 is illustrated in FIG. 10F, but no spring or biasing mechanism is shown within the recess for clarity. The coupler barrel 875 can extend from just proximal of the locking pins 874 to a distal end of the secondary extension 870. The coupler barrel 875 can include a chaffered distal radial edge to ease insertion into the dual coupler 820 as well as to smooth the surgical cord transition on the inner edge.

Figure 11A:
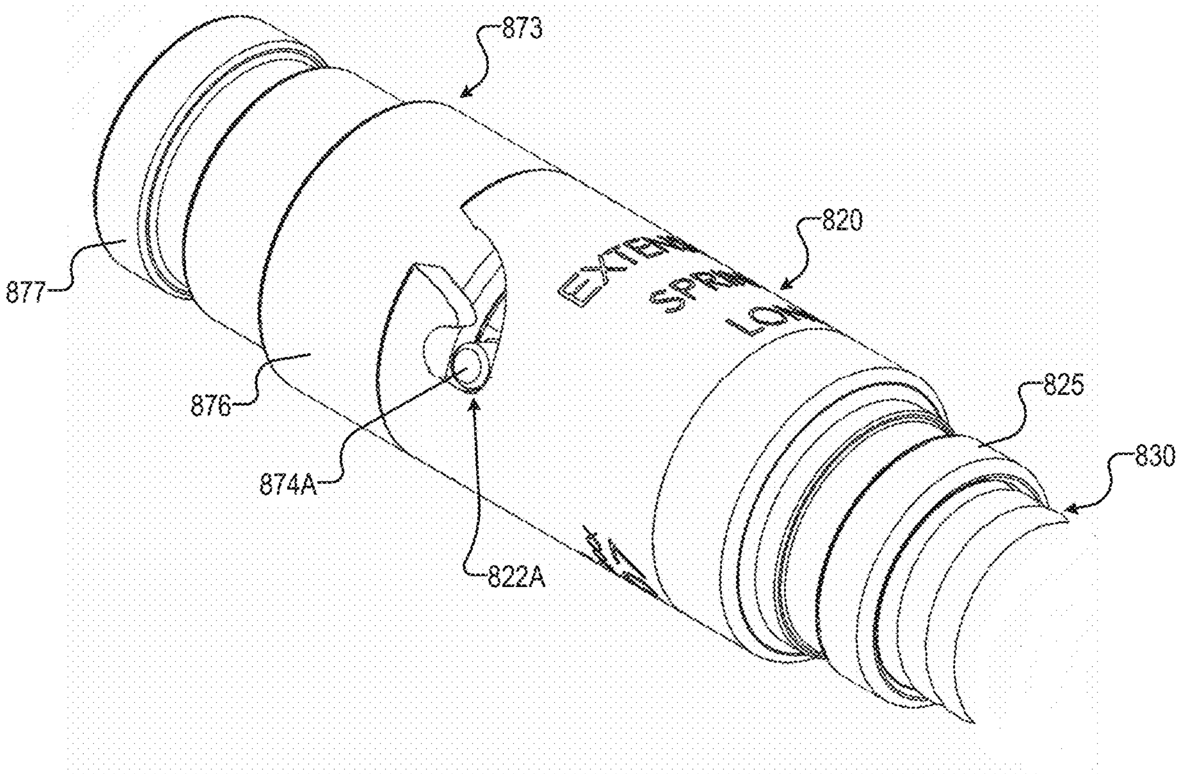
FIGS. 11A-11B are drawings illustrating a connection between a tensioner extension and a secondary tensioner extension, according to various embodiments of the present disclosure.
Figure 11B:
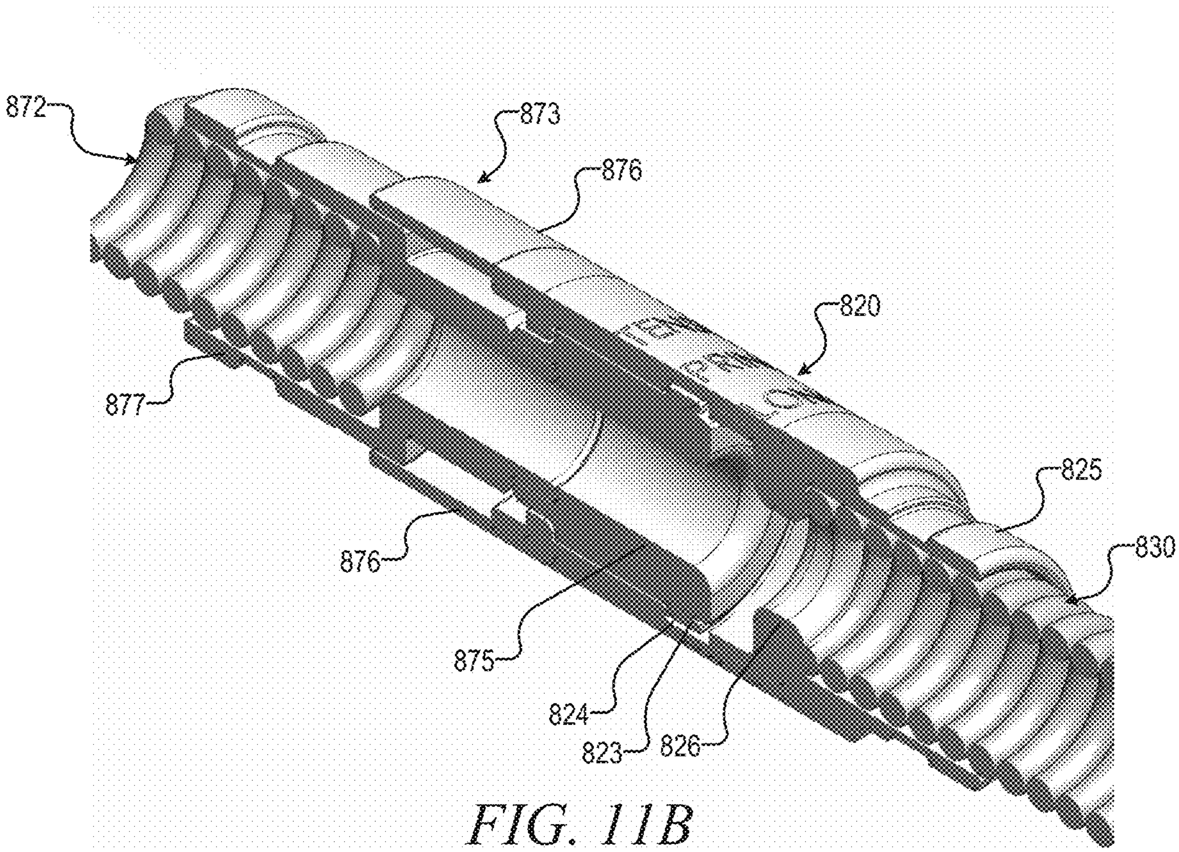

FIGS. 11A-11B are drawings illustrating the connection between the tensioner extension 810 and a secondary tensioner extension 870, according to various embodiments of the present disclosure. In this example, the dual coupler 820 is illustrated as receiving the extension coupler 873, with the locking pins 874 engaged in the P-shaped portion of the locking slots 822. The cross-sectional view illustrates the coupler barrel 875 engaging the snap ring 823 that is disposed in the ring groove 824. In certain examples, both the coupler barrel 875 and the nose assembly 710 include a detent running around the outer circumference and adapted to engage the snap ring 823 upon insertion.

Figure 12:
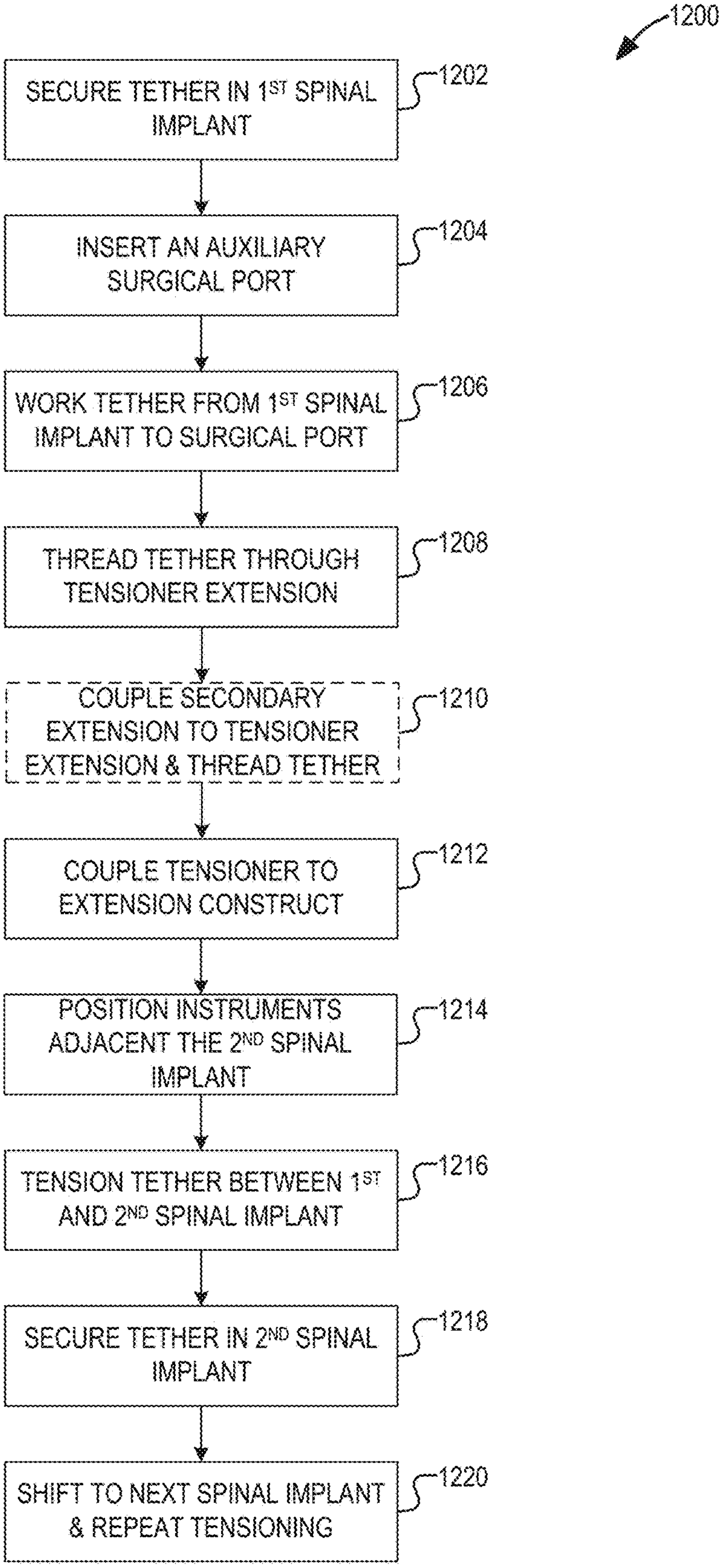
FIG. 12 is a flowchart illustrating a surgical procedure for tensioning a surgical cord utilizing a tensioner, a tensioner extension, and optionally a secondary extension, according to various embodiments of the present disclosure.

FIG. 12 is a flowchart illustrating surgical procedure 1200 for tensioning a surgical cord utilizing tensioner 702, tensioner extension 810, and optionally a secondary extension 870, according to various embodiments of the present disclosure. In this example, the surgical procedure 1200 can include operations such as: securing a cord in a $1^{st}$ spinal implant at 1202, inserting an auxiliary surgical port at 1204, working the cord from the $1^{st}$ spinal implant to the auxiliary surgical port at 1206, threading the cord through a tensioner extension at 1208, optionally coupling a secondary extension and threading the cord at 1210, coupling a tensioner to the cord tensioning instrument at 1212, positioning instrument adjacent a $2^{nd}$ spinal implant at 1214, tensioning the cord at 1216, securing the cord in the $2^{nd}$ spinal implant at 1218, and repeating the positioning and tensioning process for all remaining spinal implants at 1220. In the following discussion, the core tensioning instrument discussed can include the tensioner 702, the tensioner extension 810, and optionally the secondary extension 870. Further, throughout the disclosure the terms tether and cord are used to refer to a flexible, optionally elastic, surgical cord extendable between spinal implants, such as pedicle screws.

In this example, the surgical procedure 1200 can begin at 1202 with a surgeon working through a first surgical port, such as surgical port 805B, to secure a first end of a surgical cord to a $1^{st}$ spinal implant. The $1^{st}$ spinal implant in this example is the most superior spinal implant being used to correct the spinal deformity. Other examples may include working in an opposite direction and include use of an auxiliary surgical port that enters the patient superior to the spinal deformity. However, in the present example, an auxiliary surgical port, such as surgical port 805A, enters the patient inferior to the spinal deformity, such as in the area of the navel or a lateral position in the abdomen. The surgical procedure 1200 can continue at 1204 with insertion of an auxiliary surgical port, such as surgical port 805A. Additionally, while the surgical procedure 1200 is discussed utilizing surgical ports that operate to provide access and seal the body cavity, the surgical procedure could potentially be performed using more traditional surgical retractors. Accordingly, the type of surgical port or retractor is not material to the described operations involving the cord tensioning instrument 800. However, where surgical ports as described are necessary, such as to retain $CO_2$ within the body cavity, the cord tensioning instrument 800 further enhances a surgeon's ability to perform the required steps.

At 1206, the surgical procedure 1200 can continue with the surgeon working/maneuvering the cord from the $1^{st}$ spinal implant up through the auxiliary surgical port. At 1208, the surgical procedure 1200 can continue with the cord being threaded through a cord tensioning instrument, such as cord tensioning instrument 800 (previously referenced as cord tensioning system 800). At this stage of surgical procedure 1200, the cord tensioning instrument 800 can include at least the tensioner extension 810. At 1210, the surgical procedure 1200 can optionally include coupling a secondary extension, such as secondary extension 870, to the cord tensioning instrument 800. In an example, coupling the secondary extension 870 involves threading the secondary extension over the cord, inserting the coupling barrel 875 into the dual coupler 820, and locking the locking pins 874 into the locking slots 822. Once, the desired extension length is configured for the core tensioning instrument 800, the surgical procedure 1200 can continue at 1212 by coupling tensioner 702 onto the cord tensioning instrument 800. Note, in some examples, the surgeon may delay coupling the tensioner 702 to the core tensioning instrument 800 if maneuvering the cord within the patient is easier without the tensioner 702 attached. The tensioner 702 can be attached and detached as needed to facilitate the procedure.

At 1214, the surgical procedure 1200 can continue with the surgeon positioning instruments, such as a distal end of the cord tensioning instrument 800 and a counter tensioner 704 adjacent a $2^{nd}$ spinal implant. In this step, the distal nose member 840 of the tensioner extension 810 can be used to insert the cord into the $2^{nd}$ spinal implant and then be positioned adjacent the $2^{nd}$ spinal implant for tensioning the cord. The counter tensioning 704 can assist in positioning the cord and is also used to insert a set screw later in the procedure.

At 1216, the surgical procedure 1200 can continue with the surgeon using the cord tensioning instrument 800 to tension the cord between the $1^{st}$ and $2^{nd}$ spinal implant. Tensioning occurs through the surgeon articulating the tensioner 702, which pulls on the cord, while counter tension is carried through the tensioner extension 810 to the side of the $2^{nd}$ spinal implant (see FIG. 8A). Once the desired amount of tension has been applied, the surgical procedure 1200 can continue at 1218 with the surgeon inserting a set screw into the $2^{nd}$ spinal implant to secure the cord. In this example, the counter tensioner 704 can be utilized to deliver the set screw through a surgical port into the spinal implant.

Finally, the surgical procedure 1200 can continue at 1220 with the surgical team shifting the instruments to the next spinal implant, such as a $3^{rd}$ spinal implant, and repeating operations 1214 to 1218. One of the benefits of utilizing the cord tensioning instrument 800 involves not having to repeatedly maneuver the cord in and out of a surgical port for each spinal implant. Rather, with surgical procedure 1200 the cord is only maneuvered up through the auxiliary surgical port once. In some examples, tensioning and securing the cord to the final spinal implant, such as spinal implant 850F, may be performed using the counter tensioner 704 in combination with tensioner 702 with the cord threaded up through a surgical port positioned above the spinal implant.

Each of the above non-limiting examples can stand on its own, or can be combined in various permutations or combinations with one or more of the other examples.

Additional examples of the presently described method, system, and instrument examples include the following, non-limiting configurations. Each of the following non-limiting examples may stand on its own, or may be combined in any permutation or combination with any one or more of the other examples provided below or throughout the present disclosure.

Example 1 describes subject matter including a tensioner extension instrument. The tensioner extension instrument can include an elongate body, a dual coupler, and a nose member. The elongate body can comprise a flexible cylindrical member adapted to carry tension along a longitudinal axis of the elongate body. The flexible cylindrical member can be sized to receive a surgical cord through a lumen within the flexible cylindrical member. The dual coupler can be disposed on a proximal end of the elongate body and include a bore for receiving a nose portion of a tensioner and guiding the surgical cord into the tensioner. The nose member can be disposed on a distal end of the elongate body, and be adapted to discharge the surgical cord from the elongate body.

In example 2, the subject matter of example 1 can include the dual coupler having an internal snap ring disposed within the bore and adapted to engage a groove in the nose portion of the tensioner.

In example 3, the subject matter of example 2 can include the internal snap ring being disposed within a ring groove running around an internal circumference of the bore.

In example 4, the subject matter of example 3 can include the snap ring having a first end and a second end that form a gap within the ring groove enabling the snap ring to deform radially within the ring groove upon insertion of the nose portion of the tensioner.

In example 5, the subject matter of any one of examples 1 to 4 can include each of the nose member and the dual coupler including a compression member connecting the nose member and the dual coupler to opposite ends of the elongate body.

In example 6, the subject matter of any one examples 1 to 5 can include the dual coupler having a cord guide abutting a portion of the elongate body proximal to the compression member, the cord guide including a reduced diameter in comparison to the bore and adapted to guide the cord into the tensioner.

In example 7, the subject matter of any one of examples 1 to 6 can include the elongate body being a helical spring structure.

In example 8, the subject matter of example 7 can include the helical spring structure being a tension spring with unloaded coils that abut each other to allow the spring structure to carry a compression force created by the tension carried along the longitudinal axis without further compression of the elongate body.

In example 9, the subject matter of any one of examples 1 to 7 can include the elongate body being a flexible tubing material. In certain additional examples, the flexible tubing material can be silicone.

In example 10, the subject matter of any one of examples 1 to 9 can include the dual coupler having a locking slot adapted to receive a lock pin extending radially from a coupler barrel on a distal end of a secondary tensioner extension, where the secondary tensioner extension is adapted to add to the overall length of the tensioner extension instrument.

Example 11 describes subject matter including a system for positioning and tensioning a surgical cord. The system can include a tensioner and a tensioner extension. The tensioner can be adapted to apply a tensioning force to the surgical cord. The tensioner can comprise a nose portion including a cylindrical barrel with a central lumen to receive the surgical cord into the tensioner. The tensioner extension can be adapted to extend between the nose portion of the tensioner and a spinal implant adapted to receive the surgical cord. The tensioner extension can include an elongate body, a dual coupler, and a nose member. The elongate body can include a flexible cylindrical member to carry tension along a length of the elongate body, where the flexible cylindrical member is sized to receive a surgical cord through a lumen extending the length of the elongate body. The dual coupler can be disposed on a proximal end of the elongate body. The dual coupler can include a bore for receiving the nose portion of the tensioner and guiding the surgical cord into the tensioner. The nose member can be disposed on a distal end of the elongate body, and be adapted to discharge the surgical cord from the elongate body.

In example 12, the subject matter of example 11 can include the nose member being further adapted to abut a spinal implant upon tensioning of the surgical code through the tensioner extension.

In example 13, the subject matter of any one of examples 11 or 12 can include a secondary extension disposed between the tensioner extension and the tensioner to increase an overall length of the system.

In example 14, the subject matter of example 13 can include the secondary extension having an extension coupler, a tensioner coupler, and a short elongate body. The extension coupler can be adapted to securely couple to the dual coupler on the tensioner extension. The tensioner coupler can be adapted to receive the nose portion of tensioner. The short elongate body can include a flexible cylindrical member to carry tension along a length of the short elongate body, where the short elongate body can be positioned between the extension coupler and the tensioner coupler.

In example 15, the subject matter of example 14 can include the tensioner coupler having an internal snap ring disposed within a second bore that receives the nose portion, where the snap ring can be adapted to engage a groove in the nose portion of the tensioner.

In example 16, the subject matter of example 15 can include the internal snap ring being disposed within a ring groove running around an internal circumference of the second bore.

In example 17, the subject matter of example 16 can include the snap ring having a first end and a second end that form a gap within the ring groove enabling the snap ring to deform radially within the ring groove upon insertion of the nose portion of the tensioner.

In example 18, the subject matter of example 14 can include the extension coupler having a barrel and a locking pin extending radially outward from the barrel.

In example 19, the subject matter of example 18 can include the dual coupler having a locking slot adapted to receive the locking pin. The locking slot can include a P-shape with a lock position radially offset from an entry opening.

In example 20, the subject matter of example 19 can include the extension coupler having a bias cylinder adapted to abut a proximal end of the dual coupler to bias the locking pin into the lock position of the locking slot.

Example 21 describes subject matter including a method for positioning and tensioning a surgical cord between at least two spinal implants. In this example, the method can include a series of actions using the instrument or systems discussed in examples 1 to 20. A first action can include maneuvering a proximal end of the surgical cord from a first spinal implant to an auxiliary surgical port disposed through an incision inferior to a spinal deformity to be corrected by the surgical cord and spinal implants. A second action can include threading the surgical cord into a tensioning system including a tensioner and a tensioner extension, the tensioner extension including a flexible elongate body and a distal nose member. A third action can include maneuvering the flexible elongate body along a length of the surgical cord until the distal nose member is adjacent a second spinal implant, while a proximal end of the tensioner extension and the tensioner remain outside the auxiliary surgical port. A fourth action can include positioning the surgical cord into the second spinal implant. A fifth action can include tensioning the surgical cord between the first spinal implant and the second spinal implant by manipulating the tensioner disposed on the proximal end of the tensioner extension.

In example 22, the subject matter of example 21 can include an additional action comprising securing the surgical cord in the second spinal implant by inserting a set screw into the second spinal implant while maintaining tension on the surgical cord.

In example 23, the subject matter of example 22 can include securing the surgical cord by passing the set screw through an instrument extending through a first surgical port adjacent the spinal deformity.

In example 24, the subject matter of any one of examples 21 to 23 can include additional an action comprising maneuvering the flexible elongate body until the distal nose member is adjacent a third spinal implant, while the proximal end of the tensioner extension and the tensioner remain outside the auxiliary surgical port.

In example 25, the subject matter of example 24 can include maneuvering the flexible elongate body adjacent the third spinal implant and positioning a portion of the surgical cord in a body portion of the third spinal implant.

In example 26, the subject matter of example 25 can include positioning a counter tensioner instrument over the third spinal implant, the counter tensioner extending through a first surgical port or second surgical port adjacent the spinal deformity.

In example 27, the subject matter of any one of examples 21 to 26 can include an additional action comprising attaching a secondary extension between the tensioner and the tensioner extension prior to threading the surgical cord into the tensioning system.

In example 28, the subject matter of example 27 can include, after securing the surgical cord to the second spinal implant, detaching the secondary extension from between the tensioner and the tensioner extension, and attaching the tensioner directly to the tensioner extension.

In example 29, the subject matter of example 28 can include an additional action comprising maneuvering the flexible elongate body of the tensioner extension until the distal nose member is adjacent a third spinal implant, while the proximal end of the tensioner extension and the tensioner remain outside the auxiliary surgical port.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b) at the time of filing this application, to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention includes:

1. A method for positioning and tensioning a surgical cord in spinal implants, the method comprising:

maneuvering a proximal end of the surgical cord from a first spinal implant to an auxiliary surgical port disposed through an incision;

threading the surgical cord into a tensioning system including a tensioner and a tensioner extension, the tensioner extension including a flexible elongate body and a distal nose member;

maneuvering the flexible elongate body along a length of the surgical cord until the distal nose member is adjacent a second spinal implant, while a proximal end of the tensioner extension and the tensioner remain outside the auxiliary surgical port;

positioning the surgical cord into the second spinal implant using the tensioner extension; and tensioning the surgical cord between the first spinal implant and the second spinal implant by manipulating the tensioner disposed on the proximal end of the tensioner extension.

2. The method of claim 1, wherein the tensioner comprises:

a first aperture at the proximal end of the tensioner;

a second aperture at a distal end of the tensioner;

a channel defined between the first aperture and the second aperture, wherein the channel is able to receive the surgical cord following insertion of the surgical cord into the first aperture, and wherein the channel provides the surgical cord to the second aperture; and a first handle able to pivot relative to a second handle, wherein pivoting of the first handle between a first position and a second position relative to the second handle actuates the surgical cord through the channel, wherein the tensioner extension is able to engage with the proximal end of the tensioner, and wherein the tensioner extension is able to receive the surgical cord from the second aperture following engagement with the proximal end of the tensioner.

3. A method comprising:

securing a distal end of a surgical cord within a first spinal implant;

receiving a proximal end of the surgical cord through an auxiliary surgical port disposed through an incision;

threading the surgical cord into a tensioning system including a tensioner and a tensioner extension, the tensioner extension including a flexible elongate body and a distal nose member;

maneuvering the flexible elongate body along a first length of the surgical cord until the distal nose member is adjacent a second spinal implant, while a proximal end of the tensioner extension and the tensioner remain outside the auxiliary surgical port;

positioning the surgical cord into the second spinal implant using the tensioner extension; and tensioning the surgical cord between the first spinal implant and the second spinal implant using the tensioning system.

4. The method of claim 3, wherein tensioning the surgical cord includes manipulating the tensioner disposed on the proximal end of the tensioner extension.

5. The method of claim 3, further comprising maneuvering the proximal end of the surgical cord from the first spinal implant to the auxiliary surgical port disposed through the incision inferior to a spinal deformity to be corrected by the surgical cord and spinal implants.

6. The method of claim 3, further comprising positioning the surgical cord into a third spinal implant.

7. The method of claim 6, wherein positioning the surgical cord into the first spinal implant includes maneuvering the flexible elongate body along a second length of the surgical cord until the distal nose member is adjacent the third spinal implant.

8. The method of claim 7, wherein prior to positioning the surgical cord, the tensioner is temporarily removed from the tensioning system to enhance maneuverability of the flexible elongate body.

9. The method of claim 3, further comprising coupling a secondary tensioner extension between the tensioner extension and the tensioner to extend a length of the tensioning system.

10. The method of claim 3, wherein the tensioner comprises:

a first aperture at the proximal end of the tensioner;

a second aperture at a distal end of the tensioner;

a channel defined between the first aperture and the second aperture, wherein the channel is able to receive the surgical cord following insertion of the surgical cord into the first aperture, and wherein the channel provides the surgical cord to the second aperture; and a first handle able to pivot relative to a second handle, wherein pivoting of the first handle between a first position and a second position relative to the second handle actuates the surgical cord through the channel, wherein the tensioner extension is able to engage with the proximal end of the tensioner, and wherein the tensioner extension is able to receive the surgical cord from the second aperture following engagement with the proximal end of the tensioner.

11. A spinal tethering procedure comprising:

securing a flexible cord in a first spinal implant;

inserting an auxiliary surgical access device through an incision;

maneuvering a proximal end of the flexible cord out of a body cavity through the auxiliary surgical access device;

threading the proximal end of the flexible cord into a tensioning system, the tensioning system including a flexible elongate member;

positioning a distal end of the flexible elongate member adjacent a second spinal implant to insert a portion of the flexible cord into the second spinal implant; and tensioning the flexible cord between the first spinal implant and the second spinal implant using the tensioning system;

wherein positioning the distal end of the flexible elongate member adjacent the second spinal implant includes using a counter tensioner to assist in positioning the portion of the flexible cord into the second spinal implant.

12. The spinal tethering procedure of claim 11, wherein securing the flexible cord in the first spinal implant is performed through a first surgical access device.

13. The spinal tethering procedure of claim 12, wherein maneuvering the proximal end of the flexible cord out of the body cavity includes inserting the flexible cord into the body cavity via the first surgical access device.

14. The spinal tethering procedure of claim 11, wherein inserting the auxiliary surgical access device includes making the incision on a lateral side of the body cavity inferior to a spinal deformity to be corrected using the flexible cord and spinal implants.

15. The spinal tethering procedure of claim 11, wherein inserting the auxiliary surgical access device includes inserting one of an auxiliary surgical port and a surgical retractor.

16. The spinal tethering procedure of claim 11, wherein using the counter tensioner includes manipulating the counter tensioner through a first surgical access device.

17. The spinal tethering procedure of claim 11, wherein tensioning the flexible cord includes coupling a tensioner to a proximal end of the flexible elongate member.

18. The spinal tethering procedure of claim 17, wherein tensioning includes inserting the proximal end of the flexible cord into the tensioner and actuating the tensioner to apply a tension on the flexible cord.

19. The spinal tethering procedure of claim 17, wherein the tensioner comprises:

a first aperture at the proximal end of the tensioner;

a second aperture at a distal end of the tensioner;

a channel defined between the first aperture and the second aperture, wherein the channel is able to receive the flexible cord following insertion of the flexible cord into the first aperture, and wherein the channel provides the flexible cord to the second aperture; and a first handle able to pivot relative to a second handle, wherein pivoting of the first handle between a first position and a second position relative to the second handle actuates the flexible cord through the channel, wherein the flexible elongate member is able to receive the flexible cord from the second aperture following engagement with the proximal end of the tensioner.

20. The spinal tethering procedure of claim 11, further comprising securing the portion of the flexible cord within the second spinal implant, wherein securing the portion of the flexible cord within the second spinal implant is performed after tensioning the flexible cord using the tensioning system.

21. The spinal tethering procedure of claim 20, wherein securing the portion of the flexible cord within the second spinal implant includes inserting a set screw into a saddle portion of the second spinal implant holding the portion of the flexible cord.

22. The spinal tethering procedure of claim 11, wherein tensioning the flexible cord using the tensioning system includes positioning the distal end of the flexible elongate member against a side of the second spinal implant.

* * * * *